(12) United States Patent
Farritor et al.

(10) Patent No.: US 10,603,121 B2
(45) Date of Patent: *Mar. 31, 2020

(54) METHODS, SYSTEMS, AND DEVICES RELATING TO ROBOTIC SURGICAL DEVICES, END EFFECTORS, AND CONTROLLERS

(71) Applicant: Board of Regents of the University of Nebraska, Lincoln, NE (US)

(72) Inventors: Shane Farritor, Lincoln, NE (US); Thomas Frederick, Lincoln, NE (US); Joe Bartels, Pittsburgh, PA (US); Eric Markvicka, Brush, CO (US); Jack Mondry, Edina, MN (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 202 days.

This patent is subject to a terminal disclaimer.

(21) Appl. No.: 15/687,787

(22) Filed: Aug. 28, 2017

(65) Prior Publication Data
US 2017/0354471 A1 Dec. 14, 2017

Related U.S. Application Data

(63) Continuation of application No. 14/208,515, filed on Mar. 13, 2014, now Pat. No. 9,743,987.

(60) Provisional application No. 61/782,413, filed on Mar. 14, 2013.

(51) Int. Cl.
*A61B 34/30* (2016.01)

(52) U.S. Cl.
CPC ........ *A61B 34/30* (2016.02); *A61B 2034/302* (2016.02); *Y10S 901/28* (2013.01)

(58) Field of Classification Search
CPC ............... A61B 19/2203; A61B 34/30; A61B 2034/302
See application file for complete search history.

(56) References Cited

U.S. PATENT DOCUMENTS

| 3,870,264 A | 3/1975 | Robinson |
| 3,989,952 A | 11/1976 | Timberlake et al. |
| (Continued) | | |

FOREIGN PATENT DOCUMENTS

| CN | 1082821918 | 12/2012 |
| DE | 102010040405 | 3/2012 |
| (Continued) | | |

OTHER PUBLICATIONS

Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.

(Continued)

*Primary Examiner* — Ashley L Fishback
(74) *Attorney, Agent, or Firm* — Davis, Brown, Koehn, Shors & Roberts, P.C.; Sean D. Solberg

(57) ABSTRACT

The various embodiments disclosed herein relate to improved robotic surgical systems, including robotic surgical devices having improved arm components and/or biometric sensors, contact detection systems for robotic surgical devices, gross positioning systems and devices for use in robotic surgical systems, and improved external controllers and consoles.

20 Claims, 21 Drawing Sheets

(56) References Cited

U.S. PATENT DOCUMENTS

| | | |
|---|---|---|
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyake |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,922,755 A | 5/1990 | Oshiro et al. |
| 4,922,782 A | 5/1990 | Kawai |
| 4,990,050 A | 2/1991 | Tsuge et al. |
| 5,019,968 A | 5/1991 | Wang et al. |
| 5,172,639 A | 12/1992 | Wiesman et al. |
| 5,195,388 A | 3/1993 | Zona et al. |
| 5,201,325 A | 4/1993 | McEwen et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,388,528 A | 2/1995 | Pelrine et al. |
| 5,436,542 A | 7/1995 | Petelin et al. |
| 5,441,494 A | 8/1995 | Ortiz |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Shuichi et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyaman et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tiemey et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,497,651 B1 | 12/2002 | Kan et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |

(56) References Cited

U.S. PATENT DOCUMENTS

| | | |
|---|---|---|
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,231,610 B2 | 7/2012 | Jo et al. |
| 8,353,897 B2 | 1/2013 | Doyle et al. |
| 9,089,353 B2 | 7/2015 | Farritor |
| 9,649,020 B2 | 5/2017 | Finlay |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Azizi |
| 2002/0091374 A1 | 7/2002 | Cooper |
| 2002/0103417 A1 | 8/2002 | Gazdzinski |
| 2002/0111535 A1 | 8/2002 | Kim et al. |

(56) References Cited

U.S. PATENT DOCUMENTS

| | | |
|---|---|---|
| 2002/0120254 A1 | 8/2002 | Julien et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison |
| 2003/0100817 A1 | 5/2003 | Wang et al. |
| 2003/0114731 A1 | 6/2003 | Cadeddu et al. |
| 2003/0135203 A1 | 7/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0229338 A1 | 12/2003 | Irion et al. |
| 2003/0230372 A1 | 12/2003 | Schmidt |
| 2004/0117032 A1 | 1/2004 | Roth et al. |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0138525 A1 | 7/2004 | Saadat |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0234435 A1 | 10/2005 | Layer |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler |
| 2006/0100501 A1 | 5/2006 | Berkelman et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1 | 2/2008 | Williams |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | De La Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 7/2008 | Rioux et al. |
| 2008/0164079 A1 | 7/2008 | Ferren et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0185212 A1 | 7/2010 | Sholev |
| 2010/0198231 A1 | 8/2010 | Manzo et al. |
| 2010/0245549 A1 | 9/2010 | Allen et al. |
| 2010/0250000 A1* | 9/2010 | Blumenkranz ........ A61B 34/30 700/258 |
| 2010/0262162 A1 | 10/2010 | Omori |
| 2010/0292691 A1 | 11/2010 | Brogna |
| 2010/0318059 A1 | 12/2010 | Farritor et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0098529 A1 | 4/2011 | Ostrovsky et al. |
| 2011/0224605 A1 | 9/2011 | Farritor et al. |

(56) References Cited

U.S. PATENT DOCUMENTS

| | | |
|---|---|---|
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0264078 A1 | 10/2011 | Lipow |
| 2011/0270443 A1 | 11/2011 | Kamiya et al. |
| 2012/0029277 A1 | 2/2012 | Sholev |
| 2012/0035582 A1 | 2/2012 | Nelson et al. |
| 2012/0109150 A1 | 5/2012 | Quaid et al. |
| 2012/0116362 A1 | 5/2012 | Kieturakis |
| 2012/0179168 A1 | 7/2012 | Farritor |
| 2012/0253515 A1 | 10/2012 | Coste-Maniere et al. |
| 2013/0131695 A1 | 5/2013 | Scarfogliero et al. |
| 2013/0345717 A1 | 5/2013 | Scarfogliero et al. |
| 2014/0039515 A1 | 2/2014 | Mondry et al. |
| 2014/0046340 A1 | 2/2014 | Wilson et al. |
| 2014/0058205 A1 | 2/2014 | Frederick et al. |
| 2014/0303434 A1 | 10/2014 | Farritor et al. |
| 2015/0051446 A1 | 2/2015 | Farritor et al. |

FOREIGN PATENT DOCUMENTS

| | | |
|---|---|---|
| EP | 1354670 | 10/2003 |
| EP | 2286756 | 2/2011 |
| EP | 2286756 A1 | 2/2011 |
| EP | 2329787 | 8/2011 |
| EP | 2563261 | 3/2013 |
| JP | 5115425 | 5/1993 |
| JP | 200716235 | 6/1993 |
| JP | 2006507809 | 9/1994 |
| JP | 07 136173 | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2003220065 | 8/2003 |
| JP | 2004144533 | 5/2004 |
| JP | 2004180781 | 7/2004 |
| JP | 2004322310 | 11/2004 |
| JP | 2004329292 | 11/2004 |
| JP | 2006508049 | 3/2006 |
| JP | 2009-106606 | 5/2009 |
| JP | 2010-533045 | 10/2010 |
| JP | 2010-536436 | 12/2010 |
| JP | 2011-504794 | 2/2011 |
| JP | 2011-045500 | 3/2011 |
| JP | 2011-115591 | 6/2011 |
| JP | WO 2011/118646 A1 | 9/2011 |
| WO | WO 1992/21291 | 5/1991 |
| WO | WO 0189405 | 11/2001 |
| WO | WO 2002/082979 | 10/2002 |
| WO | WO 2002/100256 | 12/2002 |
| WO | WO 2005/009211 | 7/2004 |
| WO | WO 2005044095 | 5/2005 |
| WO | WO 2006/052927 | 8/2005 |
| WO | WO 2006 005075 | 1/2006 |
| WO | WO 2006/079108 | 1/2006 |
| WO | WO2006079108 | 7/2006 |
| WO | WO 2007011654 | 1/2007 |
| WO | WO 2007/111571 | 10/2007 |
| WO | WO 2007/149559 | 12/2007 |
| WO | WO 2009023851 A1 | 8/2008 |
| WO | WO 2009/144729 | 12/2009 |
| WO | WO2010050771 A2 | 5/2010 |
| WO | WO 2011135503 | 11/2011 |
| WO | WO 2011075693 | 7/2012 |
| WO | WO 2013009887 | 1/2013 |
| WO | WO 2014011238 | 1/2014 |

OTHER PUBLICATIONS

Allendorf et al., "Postoperative Immune Function Varies Inversely with the Degree of Surgical Trauma in a Murine Model," Surgical Endoscopy 1997; 11:427-430.

Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.

Applicant Amendment after Notice of Allowance under Rule 312, filed Aug. 25, 2008, in related case U.S. Appl. No. 11/695,944, 6pp.

Applicant Response to Office Action dated Apr. 17, 2007, in related case U.S. Appl. No. 11/552,379, filed Aug. 8, 2007, 7 pp.

Applicant Response to Office Action dated Aug. 18, 2006, in related case U.S. Appl. No. 11/398,174, filed Nov. 7, 2006, 8pp.

Applicant Response to Office Action dated Aug. 21, 2006, in related case U.S. Appl. No. 11/403,756, filed Nov. 21, 2006, 52pp.

Applicant Response to Office Action dated Oct. 29, 2007, in related case U.S. Appl. No. 11/695,944, filed Jan. 22, 2008, 6pp.

Atmel 8005X2 Core, http://www.atmel.com, 2006, 186pp.

Bailey et al., "Complications of Laparoscopic Surgery," Quality Medical Publishers, Inc., 1995, 25pp.

Ballantyne, "Robotic Surgery, Telerobotic Surgery, Telepresence, and Telementoring," Surgical Endoscopy, 2002; 16: 1389-1402.

Bauer et al., "Case Report: Remote Percutaneous Renal Percutaneous Renal Access Using a New Automated Telesurgical Robotic System," Telemedicine Journal and e-Health 2001; (4): 341-347.

Begos et al., "Laparoscopic Cholecystectomy: From Gimmick to Gold Standard," J Clin Gastroenterol, 1994; 19(4):325-330.

Berg et al., "Surgery with Cooperative Robots," Medicine Meets Virtual Reality, Feb. 2007, 1 pg.

Breda et al., "Future developments and perspectives in laparoscopy," Eur. Urology 2001; 40(1): 84-91.

Breedveld et al., "Design of Steerable Endoscopes to Improve the Visual Perception of Depth During Laparoscopic Surgery," ASME, Jan. 2004; vol. 126, pp. 1-5.

Breedveld et al., "Locomotion through the Intestine by means of Rolling Stents," Proceedings of the ASME Design Engineering Technical Conferences, 2004, pp. 1-7.

Calafiore et al., Multiple Arterial Conduits Without Cardiopulmonary Bypass: Early Angiographic Results,: Ann Thorac Surg, 1999; 67: 450-456.

Camarillo et al., "Robotic Technology in Surgery: Past, Present and Future," The American Journal of Surgery, 2004; 188: 2S-15.

Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.

Cavusiglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.

Chanthasopeephan et al., (2003), "Measuring Forces in Liver Cutting: New Equipment and Experimenal Results," Annals of Biomedical Engineering 31: 1372-1382.

Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.

Cuschieri, "Technology for Minimal Access Surgery," BMJ, 1999, 319: 1-6.

Dakin et al., "Comparison of laparoscopic skills performance between standard instruments and two surgical robotic systems," Surg Endosc., 2003; 17: 574-579.

Dumpert et al., "Improving in Vivo Robot Visioin Quality," from the Proceedings of Medicine Meets Virtual Realtiy, Long Beach, CA, Jan. 26-29, 2005. 1 pg.

Dumpert et al., "Stereoscopic In Vivo Surgical Robots," IEEE Sensors Special Issue on in Vivo Sensors for Medicine, Jan. 2007, 10 pp.

Examiner Interview Summary dated Aug. 6 and Aug. 12, 2008, in related case U.S. Appl. No. 11/695,944, 1 pg.

Examiner Interview Summary dated May 9, 2008, in related case U.S. Appl. No. 11/695,944, 1 pg.

Examiner Interview Summary dated Nov. 30, 2006, in related case U.S. Appl. No. 11/398,174, 2pp.

Falcone et al., "Robotic Surgery," Clin. Obstet. Gynecol. 2003, 46(1): 37-43.

(56) References Cited

OTHER PUBLICATIONS

Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Flynn et al., "Tomorrow's Surgery: micromotors and microbots for minimally invasive procedures," Minimally Invasive Surgery & Allied Technologies.
Franklin et al., "Prospective Comparison of Open vs. Laparoscopic Colon Surgery for Carcinoma: Five-Year Results," Dis Colon Rectum, 1996; 39: S35-S46.
Frazino, "The Laprotek Surgical System and the Next Generation of Robotics," Surg Clin North Am, 2003 83(6):.
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Grady, "Doctors Try New Surgery for Gallbladder Removal," The New York Times, Apr. 20, 2007, 3 pp.
Guber et al., "Miniaturized Instrumetn Systems for Minimally Invasive Diagnosis and Therapy," Biomedizinishe Technic. 2002, Band 47, Erganmngsband 1:.
Stoianovici et al., "Robotic Tools for Minimally Invasive Urologic Surgery", Jan. 1, 2002, pp. 1-17.
Cleary et al., "State of the Art in Surgical Rootics: Clinical Applications and Technology Challenges", "Computer Aided Surgery", Jan. 1, 2002, pp. 312-328, vol. 6.
Green, "Telepresence Surgery", Jan. 1, 1995, Publisher: IEEE Engineering in Medicine and Biology.

* cited by examiner

METHODS, SYSTEMS, AND DEVICES RELATING TO ROBOTIC SURGICAL DEVICES, END EFFECTORS, AND CONTROLLERS

CROSS-REFERENCE TO RELATED APPLICATION(S)

This application claims priority as a continuation of U.S. Pat. No. 9,743,987, entitled "Methods, Systems, and Devices Relating to Robotic Surgical Devices, End Effectors, and Controllers," which issued on Aug. 29, 2017; which claims priority to U.S. patent application Ser. No. 61/782,413, filed on Mar. 14, 2013 and entitled "Methods, Systems, and Devices Relating to Robotic Surgical Devices, End Effectors, and Controllers," both of which are hereby incorporated herein by reference in their entireties.

GOVERNMENT SUPPORT

This invention was made with government support under Grant No. DGE-10410000 awarded by the National Science Foundation: Grant Nos. NNX09AO71A and NNX10AJ26G awarded by the National Aeronautics and Space Administration: and Grant No. WSIXWF-09-2-0185 awarded by U.S. Army Medical Research and Materiel Command within the Department of Defense. The government has certain rights in the invention.

FIELD OF THE INVENTION

The various embodiments disclosed herein relate to improved robotic surgical systems, including improvements to various components therein.

BACKGROUND OF THE INVENTION

Various robotic surgical tools have been developed to perform certain procedures inside a target cavity of a patient. These robotic systems are intended to replace the standard laparoscopic tools and procedures that involve the insertion of long surgical tools through trocars positioned through incisions in the patient such that the surgical tools extend into the target cavity and allow the surgeon to perform a procedure using the long tools. As these systems are developed, various new components are developed to further improve the operation and effectiveness of these systems.

There is a need in the art for improved robotic surgical systems, including improved robotic devices and arm components, external controllers, and positioning systems.

BRIEF SUMMARY OF THE INVENTION

Discussed herein are various improvements for robotic surgical systems, including robotic surgical devices having improved arm components and/or biometric sensors, contact detection systems for robotic surgical devices, gross positioning systems and devices for use in robotic surgical systems, and improved external controllers and consoles.

In Example 1, a gross positioning system for use with a robotic surgical device comprises a base, a body operably coupled to the base, a first arm link operably coupled to the body at a first rotational joint, a second arm link operably coupled to the first arm link at a second rotational joint, and an extendable third arm link operably coupled to the second arm link. A portion of the third arm link is rotatable about a third rotational joint, and the third arm link comprises a connection component at a distal end of the third arm link. Further, the connection component is configured to be coupleable to the robotic surgical device.

Example 2 relates to the gross positioning system according to Example 1, wherein an axis of rotation of the first rotational joint is perpendicular to at least one of an axis of rotation of the second rotational joint and an axis of rotation of the third rotational joint.

Example 3 relates to the gross positioning system according to Example 1, wherein an axis of rotation of the second rotational joint is perpendicular to at least one of an axis of rotation of the first rotational joint and an axis of rotation of the third rotational joint.

Example 4 relates to the gross positioning system according to Example 1, wherein an axis of rotation of the third rotational joint is perpendicular to at least one of an axis of rotation of the first rotational joint and an axis of rotation of the second rotational joint.

Example 5 relates to the gross positioning system according to Example 1, wherein an axis of rotation of the first rotational joint, an axis of rotation of the second rotational joint, and an axis of rotation of the third rotational joint intersect at a spherical joint.

Example 6 relates to the gross positioning system according to Example 1, wherein the extendable third arm link comprises an extender body and an extendable rod slidably coupled to the extender body, wherein the extendable rod is configured to move between an extended position and a retracted position.

Example 7 relates to the gross positioning system according to Example 1, wherein the robotic surgical device comprises at least one arm, wherein the gross positioning system and robotic surgical device are configured to operate together to position the robotic surgical device within a body cavity of a patient.

In Example 8, a arm component for a robotic device configured to be positioned within a cavity of a patient comprises an arm body, a grasper end effector disposed at a distal end of the arm body, a first actuator operably coupled to the grasper end effector, and a second actuator operably coupled to the grasper end effector. The grasper end effector comprises an open configuration and a closed configuration. The first actuator is configured to actuate the grasper end effector to rotate. The second actuator is configured to actuate the grasper end effector to move between the open and closed configurations.

Example 9 relates to the arm component according to Example 8, further comprising a yoke operably coupled to the grasper end effector and a drive rod slidably disposed within the lumen of the yoke. The yoke comprises a lumen defined within the yoke, wherein the yoke is operably coupled at a proximal end to the first actuator, wherein the first actuator is configured to actuate the yoke to rotate. The drive rod is operably coupled at a distal end to the grasper end effector and at a proximal end to the second actuator, wherein the second actuator is configured to actuate the drive rod to slide between a distal and proximal position.

Example 10 relates to the arm component according to Example 9, wherein the second actuator comprises a hydraulic actuator.

Example 11 relates to the arm component according to Example 10, wherein the hydraulic actuator comprises an input port defined in the hydraulic actuator, and a piston rod slidably disposed within the hydraulic actuator. The piston rod is operably coupled to the drive rod and is configured to slide proximally when hydraulic fluid is added to the hydraulic actuator through the input port, thereby urging the drive rod proximally.

Example 12 relates to the arm component according to Example 9, wherein the second actuator comprises a pneumatic actuator.

Example 13 relates to the arm component according to Example 9, wherein the second actuator comprises a shape memory alloy ("SMA") actuator.

Example 14 relates to the arm component according to Example 13, wherein the SMA actuator comprises a distal end component and a proximal end component, at least one elongate SMA component disposed within the SMA actuator, and a tensioned spring disposed within a lumen defined in the SMA actuator. The at least one elongate SMA component is operaby coupled to the distal and proximal end components. The SMA component is configured to contract due to application of heat and thereby urge the distal component toward the proximal component, thereby urging the drive rod in a proximal direction.

Example 15 relates to the arm component according to Example 14, wherein the distal component is configured to move in a distal direction when the SMA component is allowed to contract due to removal of the heat, whereby the tensioned spring is configured to urge the distal component in a distal direction, thereby urging the drive rod in a distal direction.

In Example 16, a robotic surgical system comprises a console, a processor operably coupled to the console, a first software application operably coupled to the processor, and a robotic surgical device configured to be positioned into a body cavity of a patient. The console comprises a configurable user interface that comprises a visual display of the target surgical space, at least one overlay disposed on the user interface, and at least one deployable menu configured to appear on the user interface upon command. The at least one overlay is configured to provide information about a surgical procedure being performed. The software application is configured to generate the at least one overlay and the at least one deployable menu on the user interface.

Example 17 relates to the robotic surgical system according to Example 16, further comprising a second software application configured to provide feedback relating to a surgical performance of the user.

Example 18 relates to the robotic surgical system according to Example 16, further comprising a second software application configured to generate warm-up or practice exercises at the console for the user.

Example 19 relates to the robotic surgical system according to Example 16, further comprising at least one biometric sensor disposed on the console, and a second software application configured to utilize the biometric information to track the physiological state of the user. The at least one biometric sensor is configured to collect biometric information relating to a user.

Example 20 relates to the robotic surgical system according to Example 16, wherein the first software application is further configured to provide personalized settings for each unique user upon identification of the unique user.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 10 is a perspective view of robotic surgical device with a contact detection system, according to one embodiment.

DETAILED DESCRIPTION

Figure 8A:
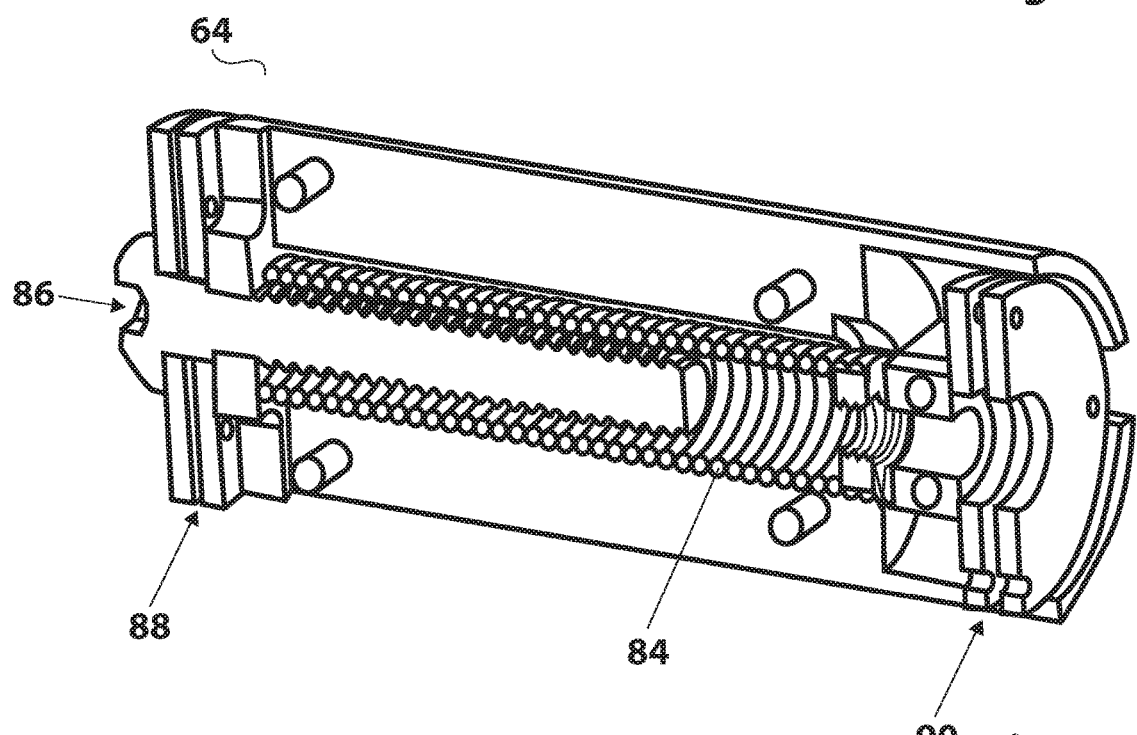
FIG. 8A is a cross-sectional perspective view of a portion of the robotic arm component of FIG. 7A.
Figure 8B:
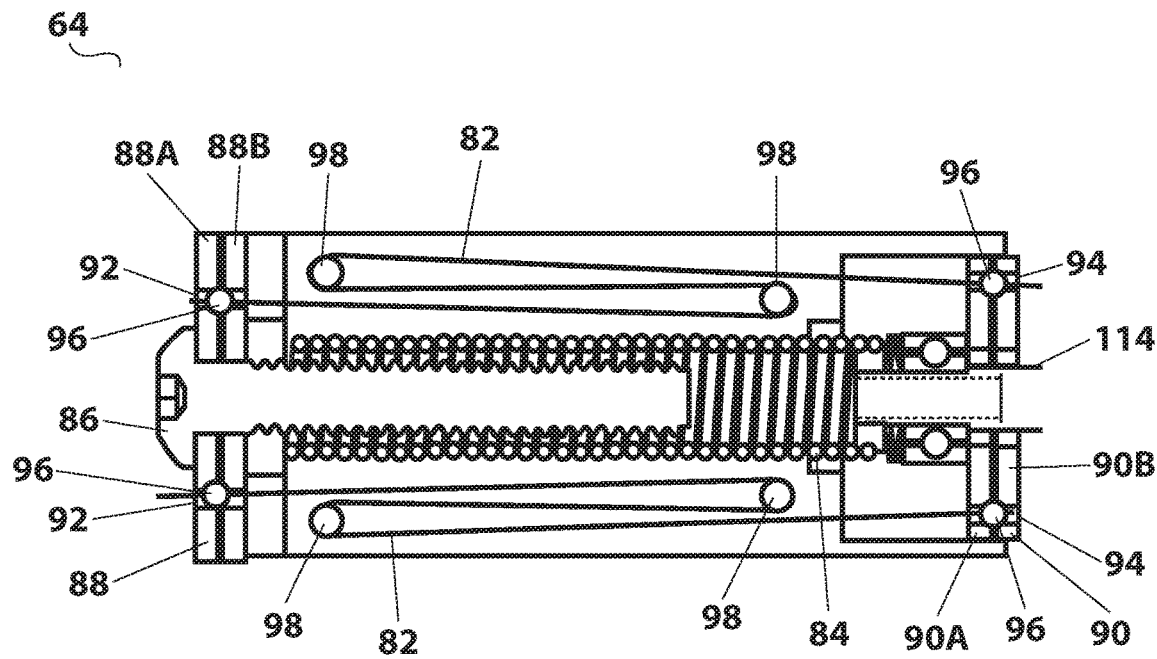
FIG. 8B is a cross-sectional side view of the portion of the robotic arm component of FIG. 8A.
Figure 8C:
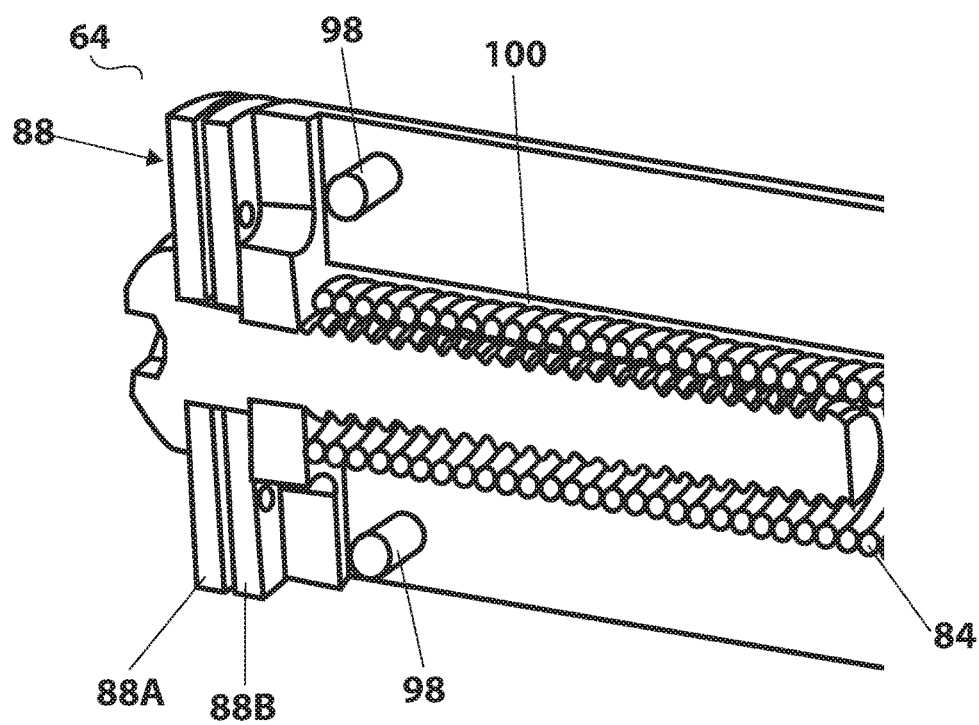
FIG. 8C is an expanded cross-sectional perspective view of a smaller portion of the robotic arm component of FIG. 8A.
Figure 8D:
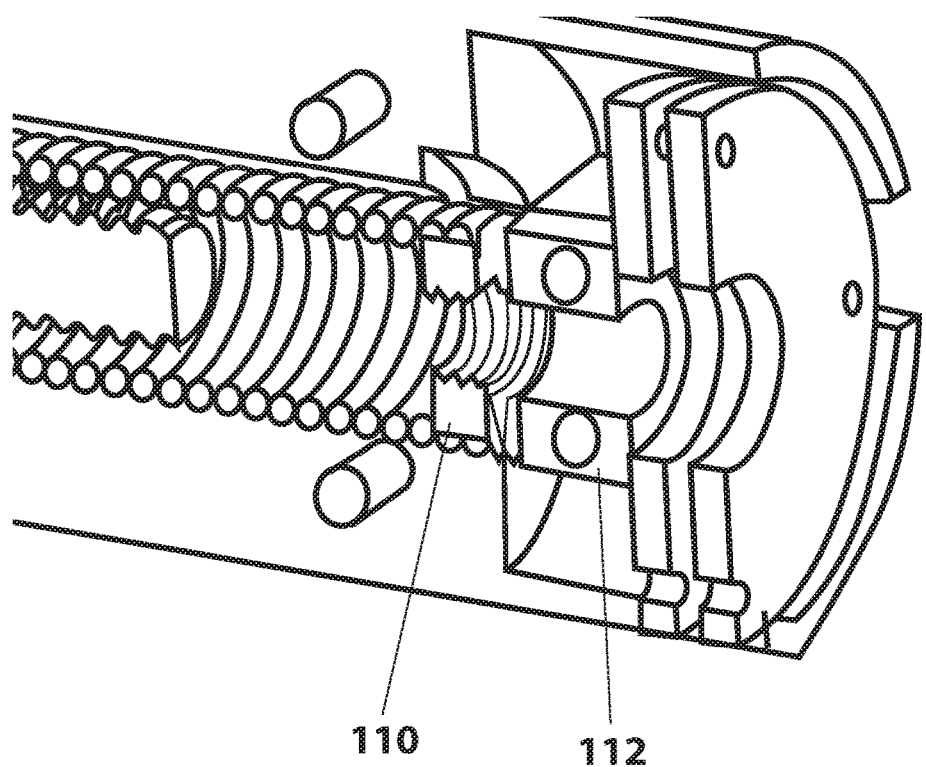
FIG. 8D is an expanded cross-sectional perspective view of another smaller portion of the robotic arm component of FIG. 8A.
Figure 9:
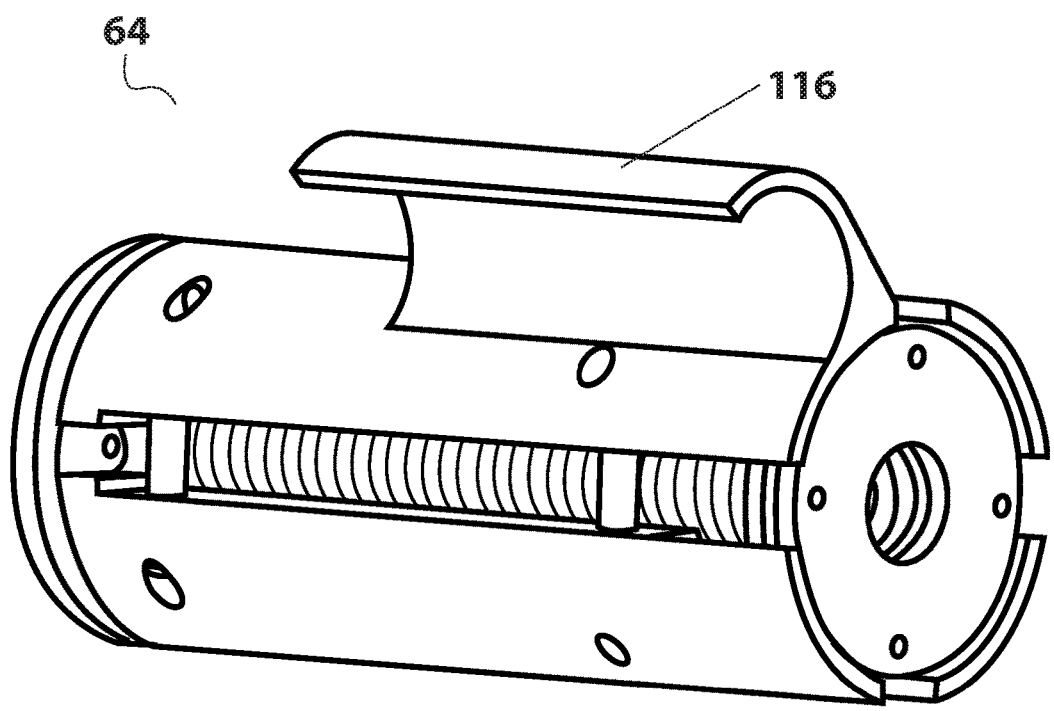
FIG. 9 is a perspective view of a portion of the robotic arm component of FIG. 7A.
Figure 10:
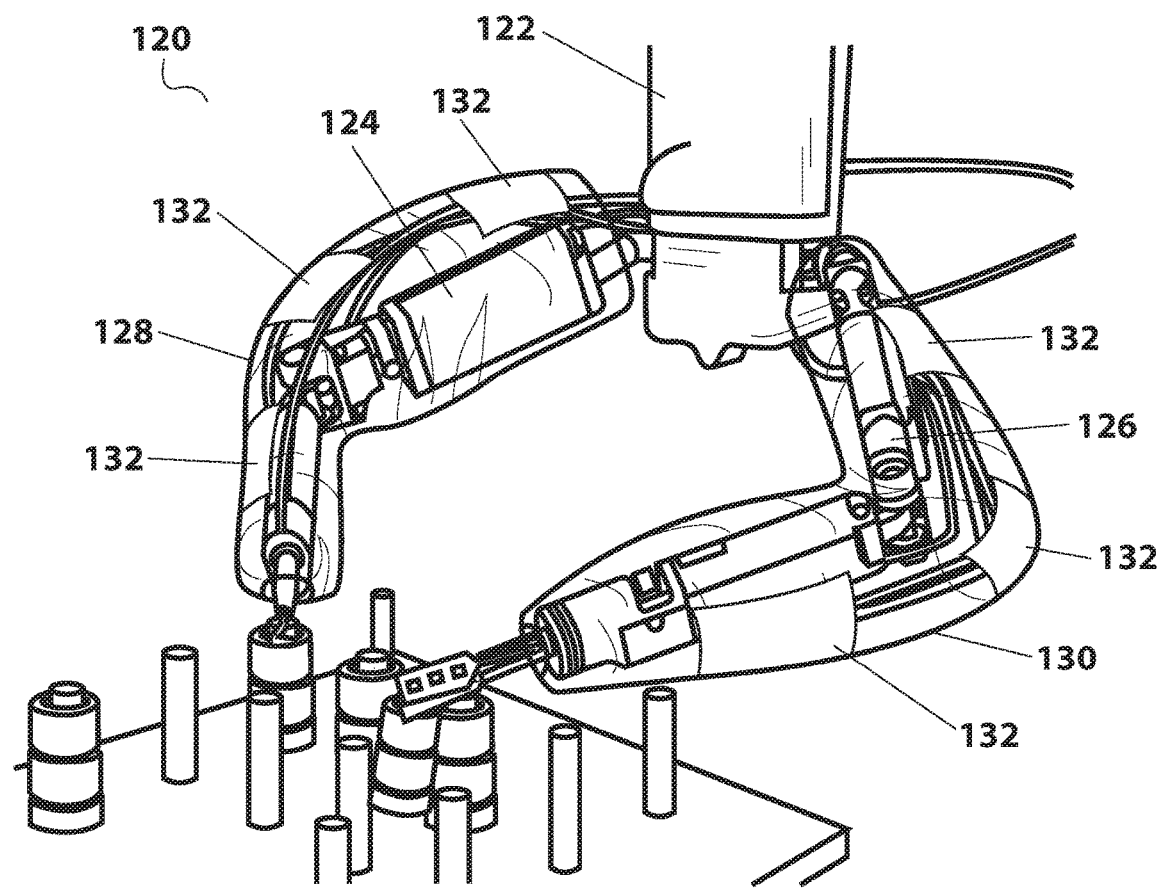
FIG. 10 is a side view of certain internal components of the robotic arm component of FIG. 1A.

FIGS. 1A-10 depict a forearm 10 having a hydraulic actuator 16, according to one embodiment. The forearm 10 has a body 12 that encases the internal components, including, as best shown in FIGS. 1B and 10, a motor 14 and a hydraulic actuator 16 (in this case, a piston 16) that are positioned within the body 12. In this embodiment, the end effector 18 at the distal end of the forearm 10 is a grasper 18. In addition, the forearm 10 also has a coupling component 20 at its proximal end that is configured to be coupleable to an upper arm (not shown) of a robotic surgical device.

In accordance with one implementation, a hydraulic actuator such as the hydraulic piston 16 in FIGS. 1A-10 can provide increased speed and force characteristics for the end effector in comparison to other types of actuators while also reducing the size requirements for the forearm. In some aspects, the increased speed and force and decreased size can be accomplished because the hydraulic actuator allows for direct linear actuation of the end effector, in contrast with threaded actuators that often require multiple gears in order to convert the rotary motion of the motor into linear motion.

Figure 2A:
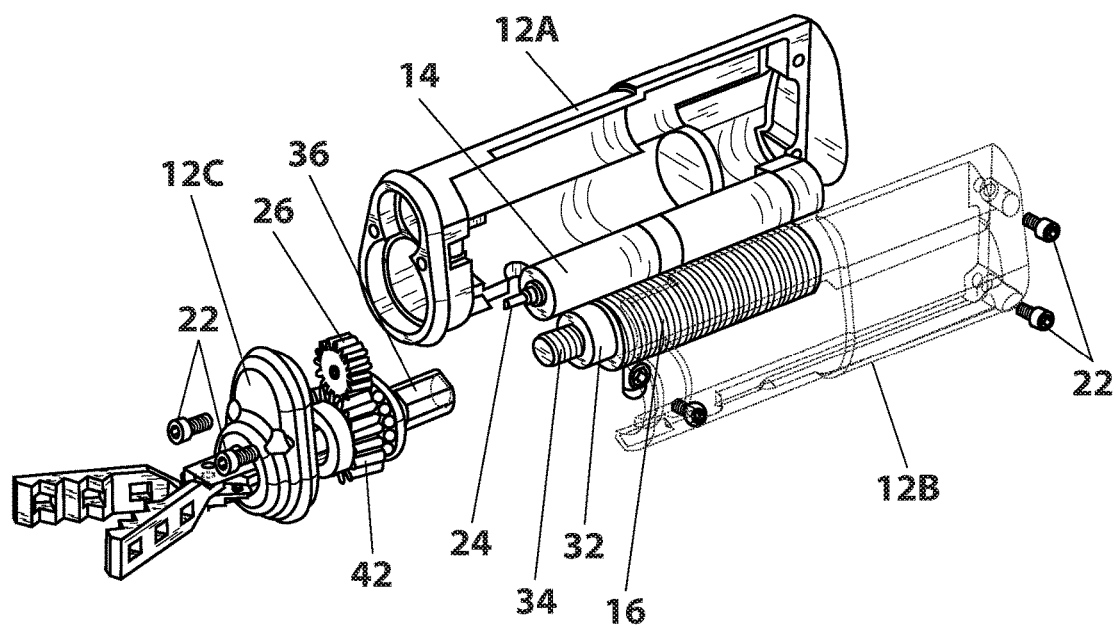
FIG. 2A is an exploded perspective view of the robotic arm component of FIG. 1A.
Figure 2B:
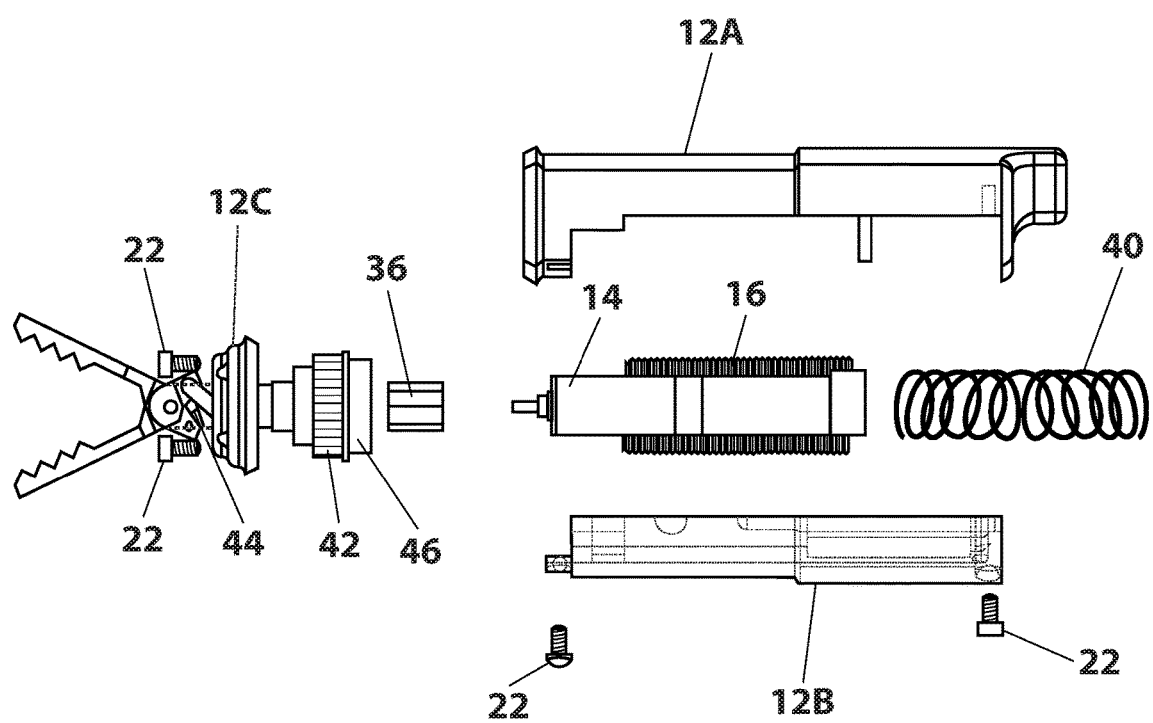
FIG. 2B is an exploded side view of the robotic arm component of FIG. 1A.

As shown in FIGS. 2A and 2B, according to one embodiment, the body 12 is made up of three body components 12A, 12B, 12C (also referred to herein as "shell components") that are configured to be coupled together to make up the body 12 (also referred to as a "shell"): a first body component 12A, a second body component 12B, and a cap component 12C. In the embodiment as shown, the first and second body components 12A, 12B is formed or configured to have form-fitting inner configurations as shown such that the motor 14 and the hydraulic piston 16 and any other interior components mate with the inner configurations when positioned within the body 12. According to one specific implementation, the second body component 12B can be transparent, thereby allowing a user to visually confirm operation of the internal components of the device. In accordance with one embodiment, the cap component 12C constrains the bearings and protects the gears during use.

In this embodiment, the coupling components 22 as best shown in FIGS. 2A and 2B couple the three body components 12A, 12B, 12C together. More specifically, the coupling components 22 in this embodiment are screws 22 that are positioned through one of the coupling components 12A, 12B, 12C and into another, thereby coupling those components together. Alternatively, the coupling components 22 can be any known devices or components for coupling two or more body components together.

Figure 1A:
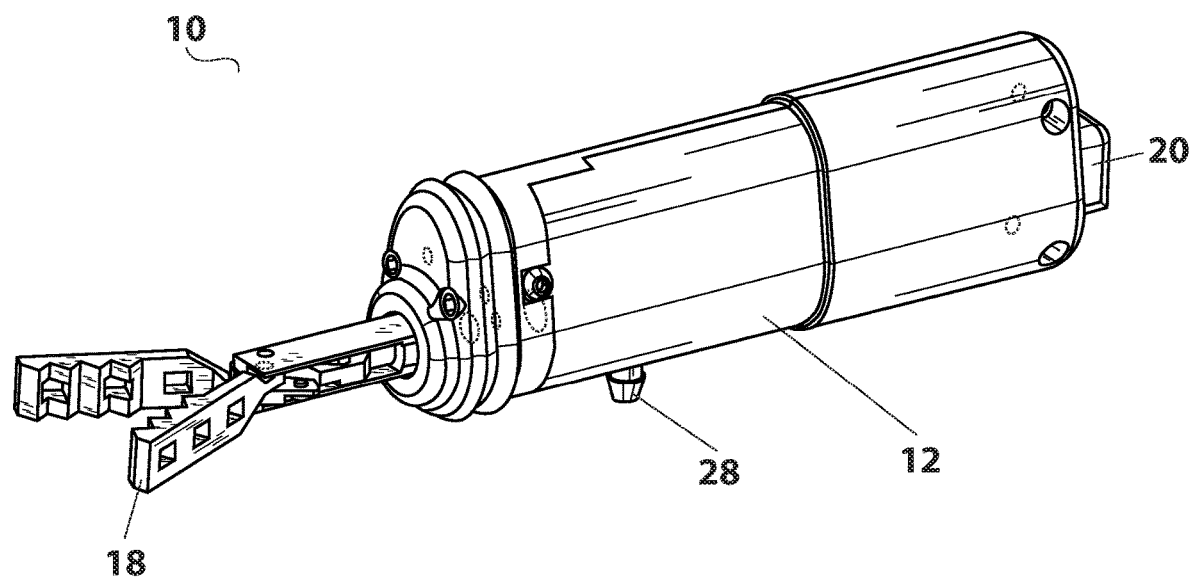
FIG. 1A is a perspective view of a robotic arm component having a hydraulic actuator, according to one embodiment.
Figure 1B:
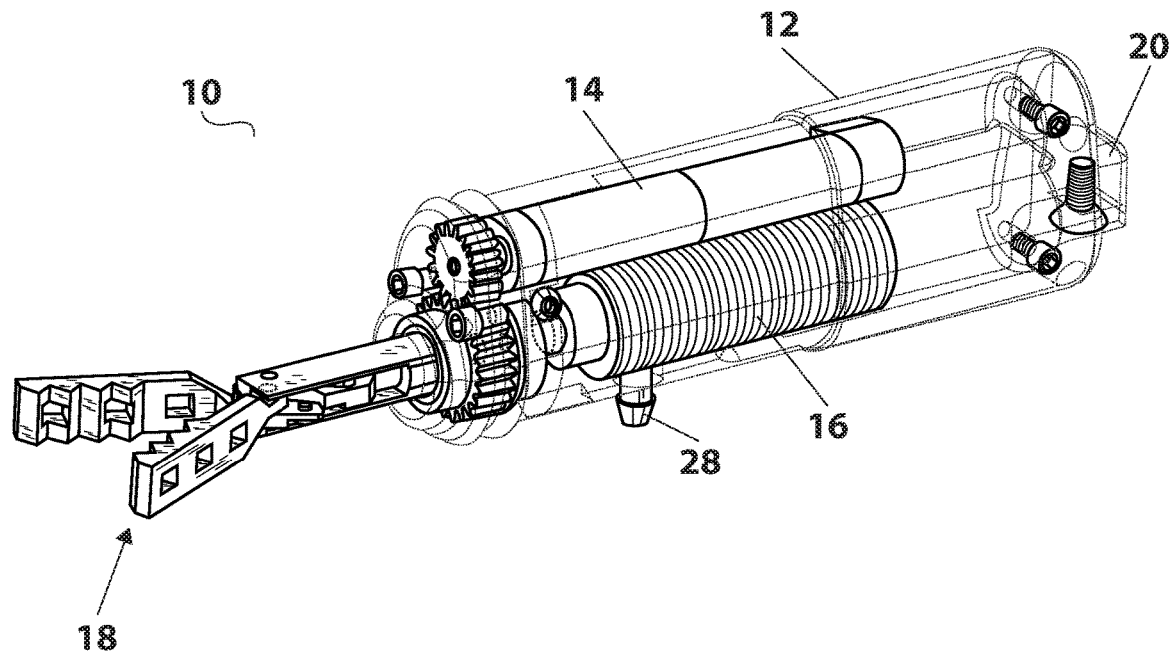
FIG. 1B is a perspective view of certain internal components of the robotic arm component of FIG. 1A.
Figure 1C:
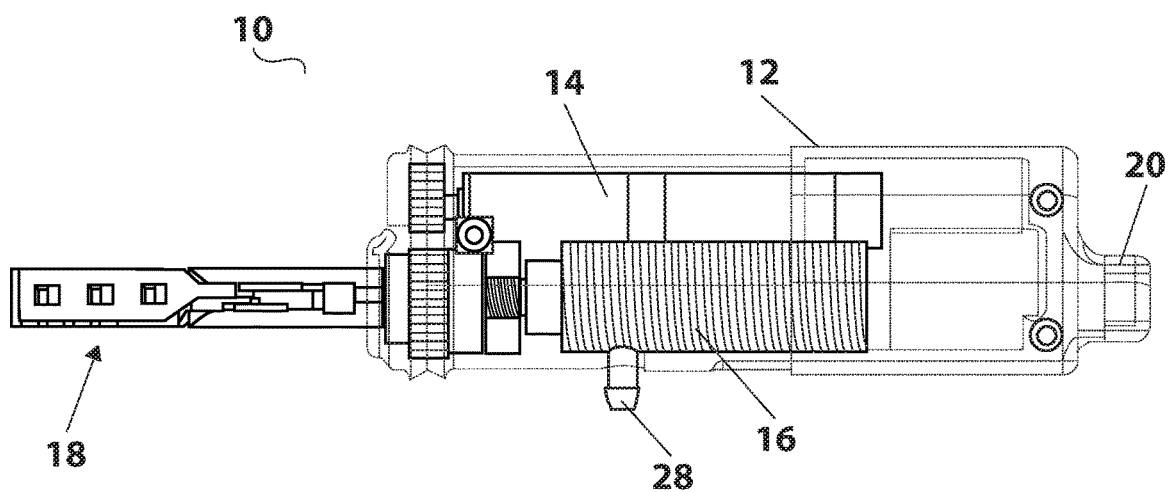
Figure 4:
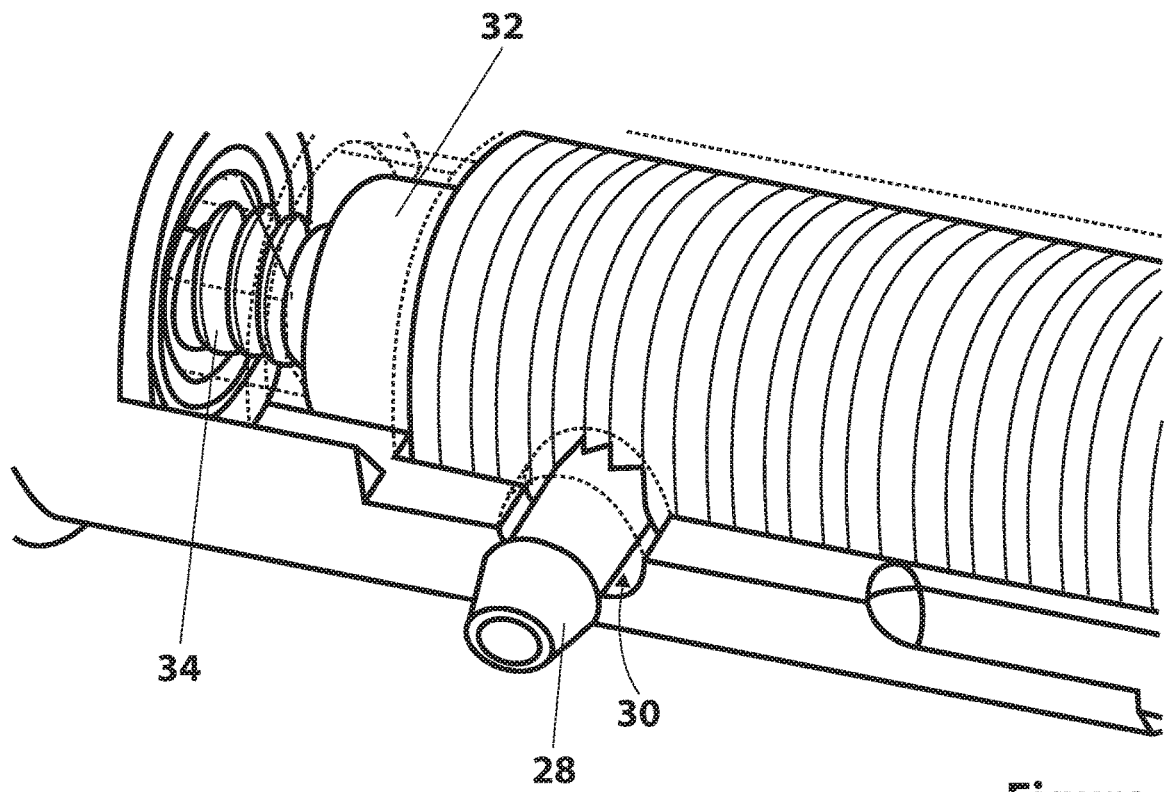
FIG. 4 is an expanded perspective view of a portion of the robotic arm component of FIG. 1A.

As best shown in FIG. 2A, the motor 14 has a drive shaft 24 at its distal end that is operably coupled to a motor gear 26 that is rotated by the motor 14 when the motor 14 is actuated. As will be explained in detail below, the actuation of the motor 14 causes the end effector 18 to rotate. Further, in this embodiment, the hydraulic piston 16 is a single acting piston having an input port 28 (also referred to as an "input barb") formed or positioned along a side of the piston 16 (as best shown in FIGS. 1B, 1C, and 4) and a spring 40 positioned at a proximal end of the piston 16 (as best shown in FIG. 2B). In one embodiment, the input port 28 is configured to be coupleable to hydraulic tubing (not shown) that is configured to provide the hydraulic fluid to the piston 16. As best shown in FIG. 4, in certain implementations the port 28 extends out of the body 12 through a hole 30 defined in the body 12.

Figure 5A:
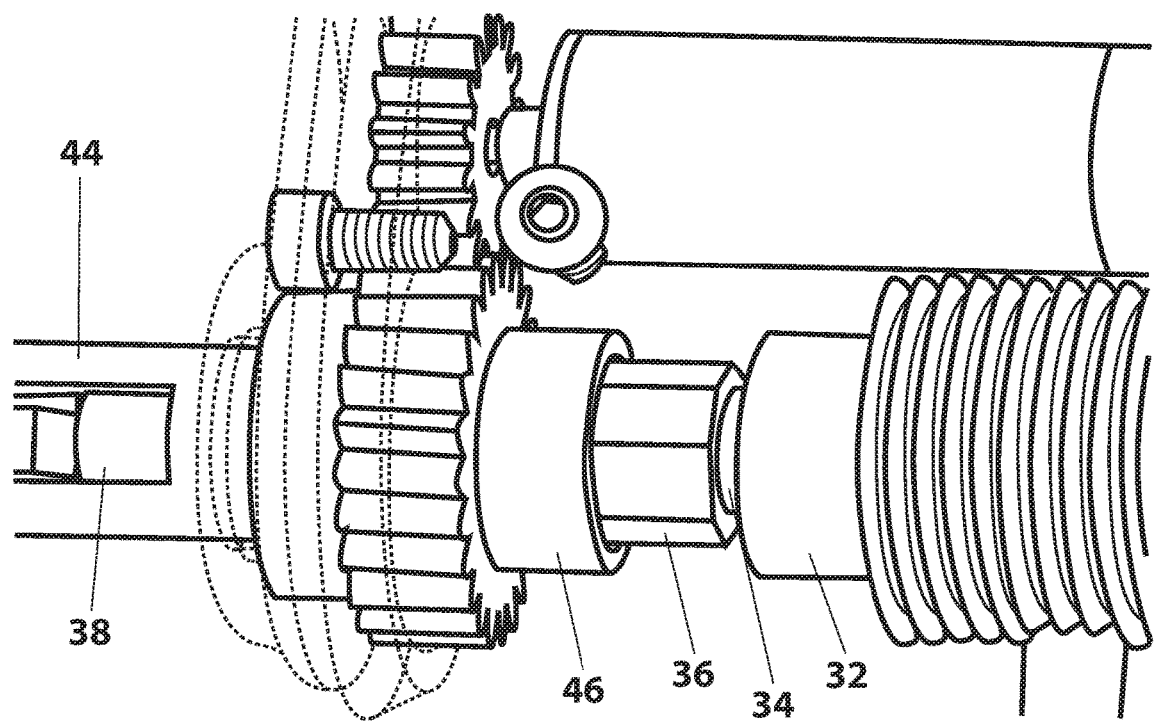
FIG. 5A is an expanded perspective view of certain internal components of the robotic arm component of FIG. 1A.
Figure 5B:
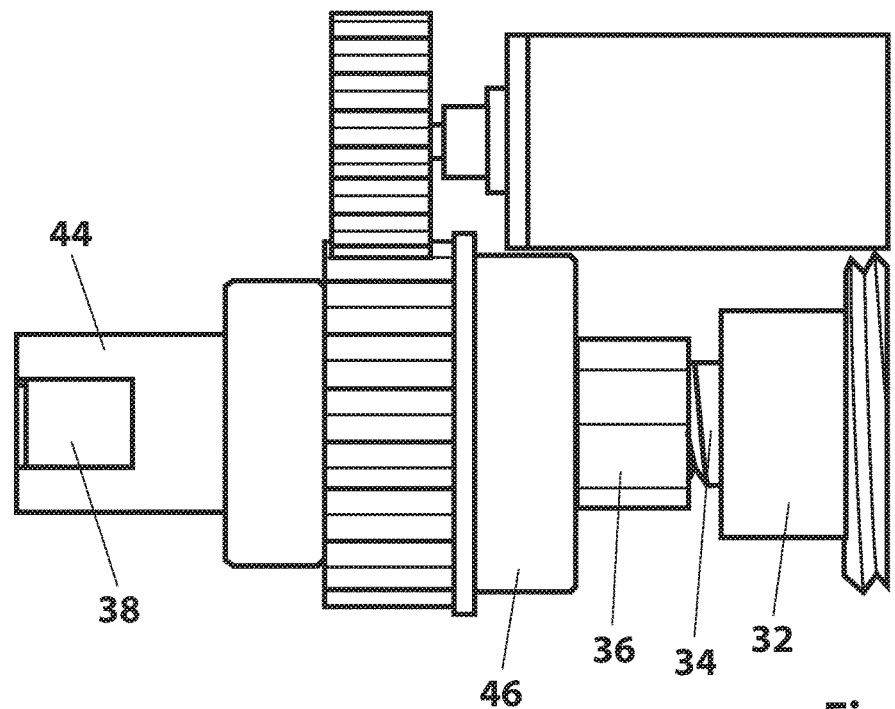
FIG. 5B is an expanded side view of the internal components of the robotic arm component of FIG. 5A.
Figure 6:
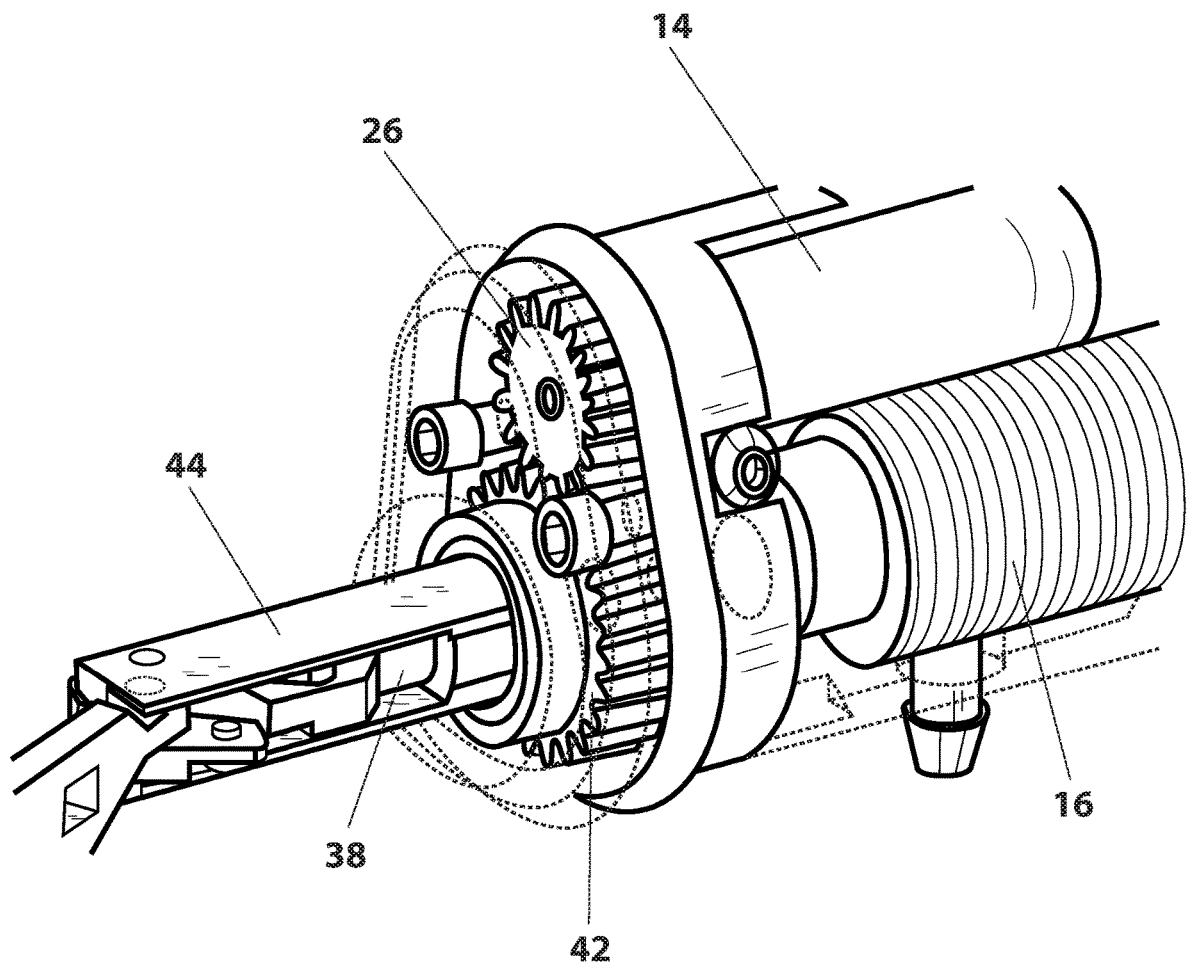
FIG. 6 is an expanded perspective view of a portion of the robotic arm component of FIG. 1A.

As best shown in FIGS. 2A, 5A, and 5B, the piston 16 is coupled to the end effector 18. In this particular embodiment, actuation of the piston 16 causes the grasper 18 to move between its open and closed positions. The piston 16 has a piston rod 32 extending from the distal end of the piston 16 with a threaded drive rod 34 coupled to and extending from the piston rod 32. The threaded drive rod 34 is threadably coupled at its distal end to a coupler 36 which, in turn, is coupled to a distal drive rod 38 that is operably coupled to the grasper arms 18. In one implementation, the coupler 36 rigidly connects the two components through the use of an adhesive such as, for example, a thread locking compound. In one specific example, the adhesive is one of the threadlocker products commercially available from Loctite®. Regardless, the adhesive retains the coupler 36 in place in relation to the threaded drive rod 34 and distal drive rod 38 such that rotation is transferred through the coupler 36 rather than unscrewing one end or the other. According to one embodiment, the coupler 36 is sized to slidably fit within the bearing 46 as described in further detail below, thereby helping to keep the overall length of the forearm short. Alternatively, the coupler 36 need not be sized to fit within the bearing 46. Regardless, actuation of the piston 16 can actuate the grasper arms 18 to open and close.

Figure 3:
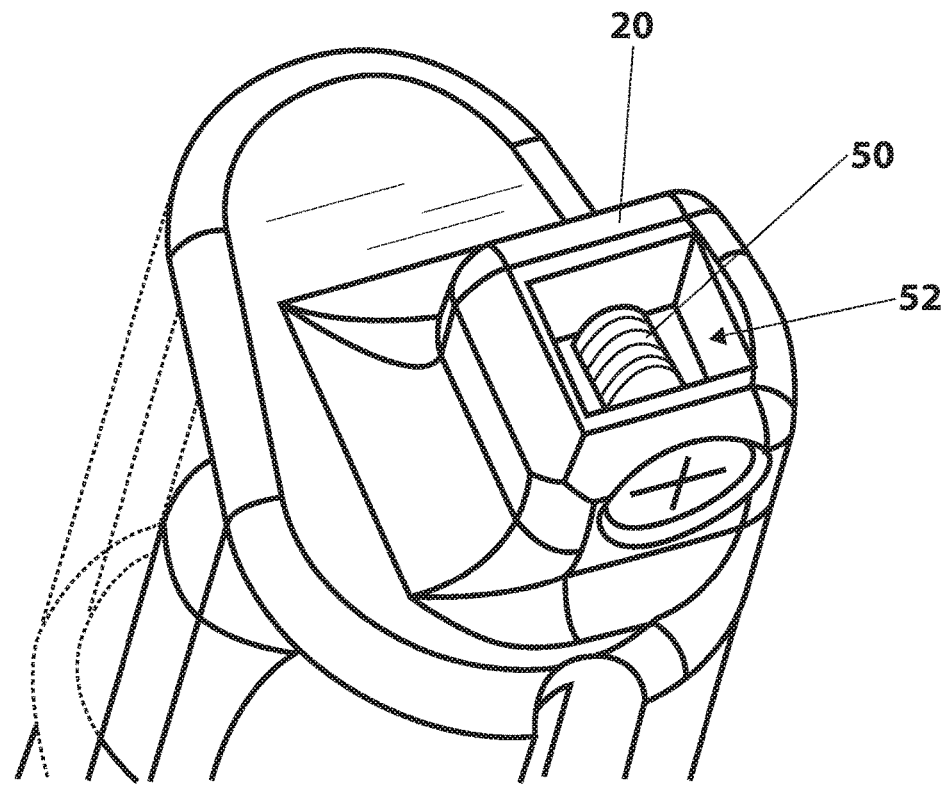
FIG. 3 is an expanded perspective view of a portion of the robotic arm component of FIG. 1A.

FIG. 3 depicts the proximal end of the forearm body 12 and the coupling component 20. It is understood that the coupling component 20 can be any known device or component for rigidly coupling one portion of a medical device to another at a joint, and is specific to the upper arm (not shown) to which the forearm body 12 is being coupled. In this embodiment, the coupling component 20 is a rectangular protrusion 20 having a retention bolt 50 disposed within the square opening 52 defined within the protrusion 20. In accordance with one implementation, the protrusion 20 is formed at the proximal end of the first body component 12A such that rigidity may be maintained from the coupling component 20 to the end effector 18.

In use, the piston 16 operates as follows, according to one embodiment. It is understood that, according to certain implementations, the grasper 18 operates in the same fashion as many known graspers, with the distal drive rod 38 slidably positioned within a lumen (not shown) defined in the yoke 44 such that rod 38 (which is operably coupled to the arms of the grasper 18) can actuate the grasper to move between its open and closed configurations by sliding the rod 38 distally and proximally in relation to the yoke 44. To actuate this grasper 18 or any other known grasper requiring lateral actuation, fluid is added to the piston 16 through the port 28, which is best shown in FIGS. 1A, 1B, 10, and 4.

Referring specifically to FIG. 4, the port 28 is positioned along the piston 16 such that the increased pressure causes the piston rod 32 to move proximally (back into the piston body 16). This movement of the rod 32 pulls the threaded drive rod 34 and the coupler 36 in a proximal direction, thereby pulling the distal drive rod 38 proximally as well, thereby causing the grasper arms 18 to move toward the closed position. To actuate the grasper arms 18 toward the open position, the pressure in the piston 16 is reduced, thereby allowing the spring 40 to urge the piston 16 in the distal direction, thereby urging the piston rod 32, the threaded drive rod 34, the coupler 36, and the distal drive rod 38 distally and thus urging the grasper arms 18 toward the open position.

In one embodiment, the piston 16 is a single-action piston 16 with the port 28 positioned such that increased pressure causes the piston rod 32 to move proximally as described above. This configuration eliminates the need for an excessively strong fluid vacuum to move the piston proximally. A piston that requires such a strong vacuum can have problems if any air leaks into the system and can lead to more air entering the fluid tract.

In one embodiment, the fluid provided to the piston 16 through the port 28 is provided by a driving mechanism (not shown). The driving mechanism can be any known device or component that can be coupled to the port and thereby provide fluid to the piston 16 at varying levels of pressure. According to one implementation, the driver can also be configured to sense the applied pressure and regulate the pressure in the piston 16 to drive the end effector 18 motion based on force at the end effector 18 rather than position of the end effector.

In accordance with one implementation, the fluid in the hydraulic system can be water, saline, or any other known biosafe noncompressible fluid.

Alternatively, the piston 16 can be a dual acting piston that can provide better control of the position and performance of the piston.

In the embodiment as shown, the end effector 18 can also be rotated via the motor 14. That is, as mentioned above, the motor 14 can be actuated to cause the end effector 18 to rotate. As best shown in FIGS. 2A and 2B, the motor 14 rotates the motor shaft 24, which rotates the motor gear 26, which, in turn, rotates the driven gear 42. The driven gear 42 is rotationally coupled to the end effector 18 such that rotation of the driven gear 42 causes rotation of the end effector 18. More specifically, the driven gear 42 is coupled to the yoke 44 such that rotation of the drive gear 42 causes rotation of the yoke 44. In one embodiment, the gear ratio of the motor gear 26 and the driven gear 42 can be changed to provide different performance characteristics of the end effector 18 roll axis.

The rotation by the motor 14 as described above is decoupled from the push/pull motion of the piston rod 32. That is, the components that are used to cause the rotation and the push/pull motion are configured such that the two actions are separate and independent from each other. In this embodiment, the decoupling results from the bearing 46 that is rotationally coupled to the driven gear 42 such that rotation of the driven gear 42 causes the bearing 46 to rotate. The bearing 46 further is rotatably positioned over the coupler 36 and distal drive rod 38 such that the coupler and distal drive rod 38 are positioned through the bearing 46 and do not rotate when the bearing 46 rotates. Thus, the distal drive rod 38 can move distally and proximally while the bearing 46 rotates.

In one alternative embodiment, the hydraulic actuation can be replaced with pneumatics, shape memory alloy, or some other linear actuation component.

In accordance with an alternative implementation, a shape memory alloy is used to actuate the end effector. FIGS. 7A-9 depict a forearm 60 having an end effector 62 that is actuated using a shape memory alloy that contracts upon heating.

Figure 7A:
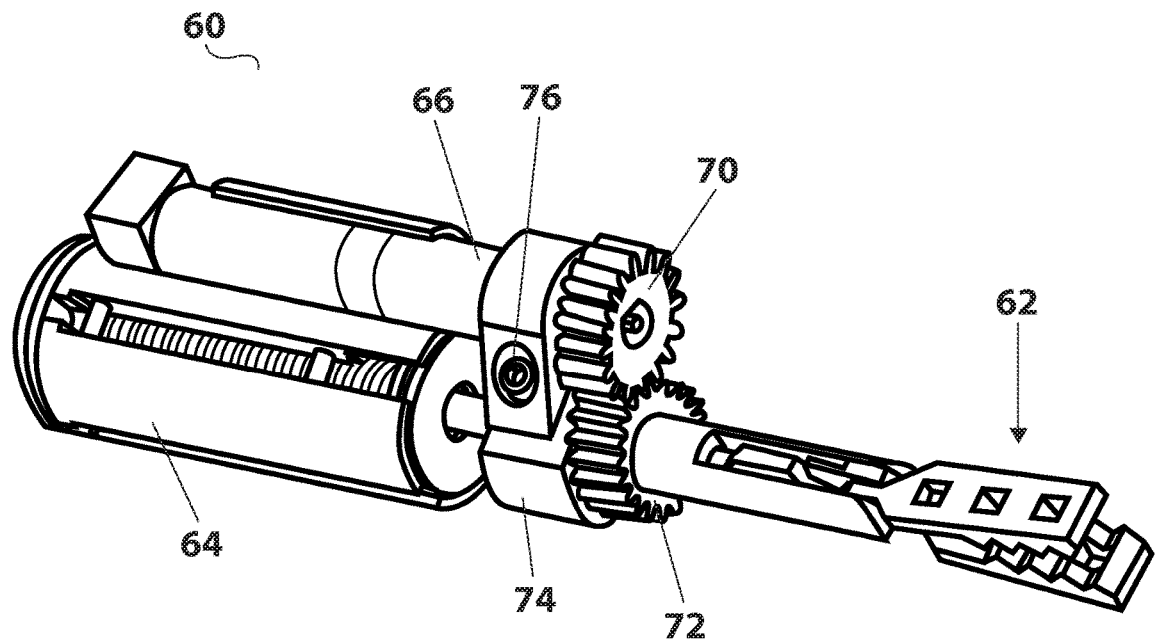
FIG. 7A is a perspective view of a robotic arm component having a shape memory alloy actuator, according to one embodiment.
Figure 7B:
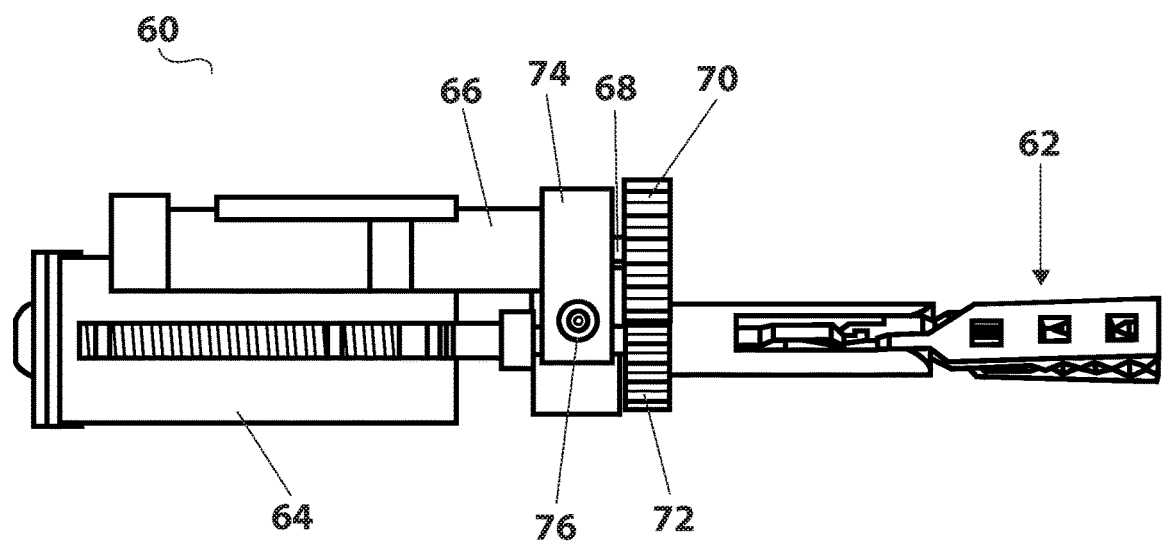
FIG. 7B is a side view of the robotic arm component of FIG. 7A.
Figure 7C:
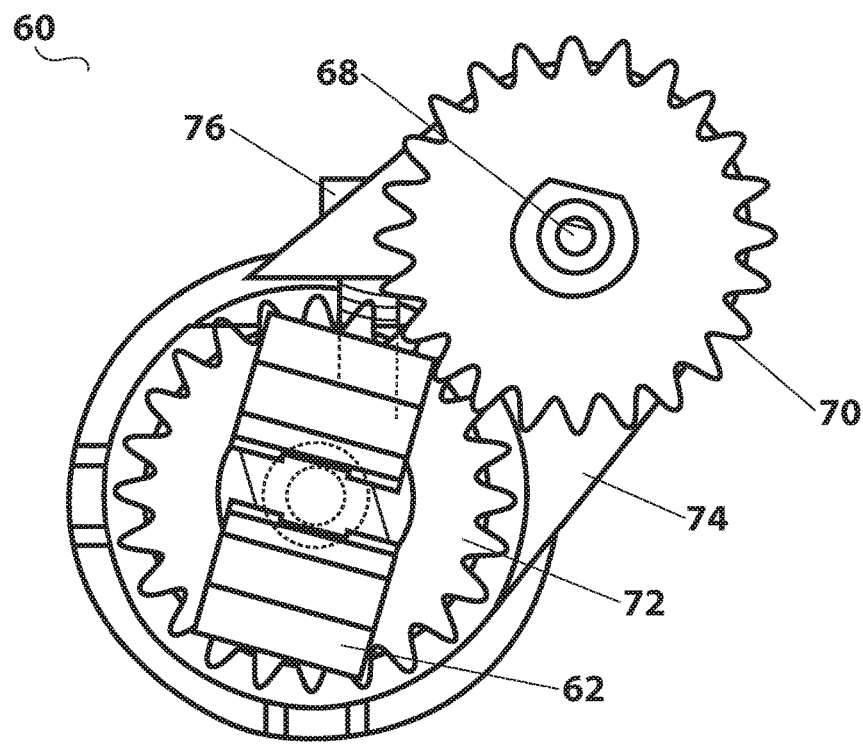
FIG. 7C is a cross-sectional view of a portion of the robotic arm component of FIG. 7A.

As shown in FIGS. 7A-7C, the end effector 62 in this implementation is a set of graspers 62. The forearm 60 has a shape memory alloy ("SMA") actuator 64 that is operably coupled to the graspers 62 such that actuation of the SMA actuator 64 causes the graspers 62 to move between its open and closed positions. Further, the forearm 60 also has a motor 66 that is operably coupled with the grasper 62 such that actuation of the motor 66 causes the grasper 62 to rotate. As best shown in FIGS. 7B and 7C, the motor 66 has a motor shaft 68 that is operably coupled to a motor gear 70. The motor gear 70 is operably coupled to a driven gear 72 that is, in turn, operably coupled to the graspers 62.

According to one embodiment, the graspers 62 are identical or substantially similar to the graspers 18 described in detail above. Alternatively, any known grasper configuration or any other known end effector can be used.

In one implementation, the forearm 60 has a gearbox 74 that is operably coupled to motor 66, the motor gear 70, and the driven gear 72 such that the gearbox 74 is configured to maintain the relative position between the motor gear 70 and the driven gear 72, thereby ensuring that the motor gear 70 will maintain a uniform contact distance with the driven gear 72. According to one embodiment, the gearbox 74 has a clamping feature actuated through the tightening of a bolt 76. The tightening of the bolt 76 pulls the motor gear 70 and driven gear 72 together and further secures the motor 66, thereby helping to prevent rotation or translation of the motor 66 or any other components.

FIGS. 8A-8D are a set of cutaway figures depicting the SMA actuator 64 according to one embodiment. The actuator 64 provides linear motion to move the grasper 62 between its open and closed positions. According to one implementation, as best shown in FIG. 8B, the SMA actuator 64 has two SMA wires 82 that are configured to contract upon heating. As used herein, the term "SMA wire" is intended to mean any elongate shape memory alloy component (also referred to as a "cord," "rope," or "braid") that can be used with the SMA actuator 64 as disclosed or contemplated herein. The actuator 64 also has a spring 84 positioned through a central lumen 100 of the actuator 64.

According to one embodiment, the SMA material used in the wires 82 is nitinol. Alternatively, the material is a copper-based SMA material or a ferromagnetic shape-memory alloy ("FSMA") material. In a further alternative, the material is a shape-memory polymer such as, for example, a shape-memory plastic. In yet another alternative, the shape-memory material can be any known shape-memory material that can be used in a medical device. Further, alternative implementations of the actuator 64 can be made of any material or component that can change its physical structure in a repeatable and useful way.

As best shown in FIGS. 8A and 8B, the actuator 64 also has two end components 88, 90 and a bolt 86 inserted into the proximal end of the actuator 64 such that the bolt is positioned within the central lumen 100 and within the spring 84, thereby helping to constrain the spring 84 within the actuator 64. The bolt 86 helps to retain the proximal end component 88 in place. In one embodiment, each of the end components 88, 90 is made up of two components (such as, for example, circuit boards) that are coupled together to make a single end component 88, 90. That is, as best shown in FIG. 8B, the proximal end component 88 has a first end component 88A and a second end component 88B, while the distal end component 90 has a first end component 90A and a second end component 90B. Each of the end components 88, 90 has two openings 92, 94 defined within the component 88, 90, with each opening 92, 94 configured to receive one of the SMA wires 82. In accordance with one implementation, each of the SMA wires 82 is configured to be formed into a knot 96 that helps to couple the wires 82 to the end components 88, 90 in the openings 92, 94 such that the wires 82 are fixedly coupled to the end components 88, 90 while also maintaining an electrical connection between the wires 82 and the end components 88, 90.

In one embodiment, with reference to one wire 82 being coupled to the distal end component 90 (with the understanding that the same process is used for each opening 92, 94 in each end component 88, 90), the wire 82 is positioned through the opening 94 and then a knot 96 is tied into the wire 82 and positioned between the first component 90A and the second component 90B of the distal end component 90. The knot tail is then fed through the opening of the second component 90B and an adhesive or fixative is used to fix the first and second components 90A, 90B together to form the distal end component 90, thereby capturing the knot 96 within the end component 90.

In accordance with one implementation, each opening 94 has a conductive ring around the opening 94 that helps to establish the electrical connection with the wire 82 disposed through the opening 94. It is understood in the art that such rings are standard features of circuit boards.

Alternatively, the two end components 88, 90 can be any devices or components that can retain the wires 82 in place while also providing an electrical connection to the wires 82. Further, instead of a knot, any known attachment component or mechanism that secures the wire 82 to the end component 88, 90 while also maintaining an electrical connection can be used.

According to one implementation, the actuator 64 also has four bolts or pins 98 positioned strategically within the actuator 64 such that the two SMA wires 82 can be positioned around the pins 98 as shown in FIG. 8B. More specifically, the pins 98 are positioned such that each wire 82 can be looped around the pins 98 in a fashion that increases the length of the wire 82 in the actuator 64 (in comparison to the length of the wire if there were no pins) while preventing the wires 82 from contacting each other and thus causing a short-circuit. The longer the wire 82, the greater the amount of force that can be created by the actuator 64. According to one embodiment in which a type of nitinol is used for the SMA wires 82, the nitinol wires 82 shortens in an amount equaling about 4% of its total length. In such an embodiment, the length of the wires 82 must be maximized using the pins 98 to loop the wires 82 in order to achieve the amount of pull required for the actuator 64. Thus, if more force is required to ensure that the grasper 62 can be moved between its open and closed positions, then the length of the wire 82 within the actuator 64 can be increased by looping the wire 82 around the pins 98 as shown, especially given the need to keep the overall size of the forearm and thus the actuator 64 as small as possible. Of course, the amount of force required, and thus the length of the wire 82 that is needed, will vary based on the type of shape memory alloy that is used for the wire 82 and the type of end effector 62 that is used. In certain alternatives, a different SMA wire 82 or a different type of nitinol can be used that has the capacity to contract more than the nitinol wires 82 described above.

As best shown in FIG. 8D, the actuator 64, in one embodiment, also has a nut 110 and a bearing 112. The nut 110 is configured to receive and be threadably coupled to the drive rod 114 (as best shown in FIG. 8B) that is operably coupled to the end effector 62. Alternatively, instead of a nut, any other coupling component or mechanism can be used to couple the actuator 64 to the end effector 62. The bearing 112 is positioned to decouple the rotation of the end effector 62 (which is actuated by the motor 66 as discussed above) from the linear motion that is actuated by the SMA actuator 64.

In accordance with one implementation, the wire 82 is designed to be able to withstand a certain minimum amount of pull force. Further, as shown in FIGS. 8A-8D, the actuator 64 has two wires 82 that are used together to create the appropriate amount of total force for the actuator 64. Alternatively, three or more wires 82 could be incorporated into the actuator 64 to provide additional actuation force. In a further alternative, two or more wires 82 could be braided together into bundles.

In one embodiment, the wire 82 is actually a braided wire 82 having four braided strands. According to one implementation, the four braided strands provide sufficient strength such that the appropriate amount of force can be applied to the wire 82 without breaking the wire 82. In addition, the four strands in the wire 82 also make it possible to provide two separate electrical loops, such that, for example, the power passes up strand one, down strand two, up strand three, and down strand four.

FIG. 9 depicts an embodiment of an SMA actuator 64 having a coupling component 116 disposed on an exterior portion of the actuator 64. In the specific embodiment as shown, the coupling component 116 is a curved projection 116 configured to couple with the motor 66 discussed above such that the motor 66 fits or "nests" within the concave portion of the projection 116. The coupling component 116 prevents the rotational actuation of the motor 66 from causing the motor 66 and actuator 64 to rotate in relation to each other.

In use, according to one embodiment, the SMA wires 82 are actuated by applying heat to the wires 82 via a known process in which an electrical current is applied to the wires, which creates heat that causes the wires 82 to contract. The contraction of the wires 82 applies a pulling force on the distal end component 90, thereby causing the component 90 to be urged proximally, which causes the drive rod 114 (shown in FIG. 8B) to retract (move in a proximal direction), thereby actuating the grasper 62 to move between its closed and open positions. In one embodiment, the retraction of the drive rod 114 causes the grasper to move toward its closed position. Alternatively, any known process for applying heat can be used.

When the grasper 62 needs to be actuated to move to the other position, the heat being applied to the SMA wires 82 is removed and the wires 82 are allowed to cool. As they cool, they begin to expand and thus lengthen. The spring 84 within the actuator 64 is configured to provide the restoring force that urges the distal end component 90 in a distal direction, thereby urging the drive rod 114 in the same direction and thus actuating the grasper 62 to move toward the other position. In one implementation, the urging of the drive rod 114 in the distal direction causes the grasper to move toward its open position.

In accordance with one embodiment, the SMA actuator 64 has channels defined within the actuator that provide fluidic communication between the interior and the exterior of the actuator 64, thereby allowing ambient air to flow into the interior of the actuator 64 and into contact with the SMA wires 82, thereby providing natural convective cooling of the wires 82. Alternatively, active cooling can be provided, such as forced air or thermo-electric cooling (such as, for example, Peltier coolers, one version of which is commercially available from Beijing Huimao Cooling Equipment Co., Ltd., located in Beijing, China) (not shown), both of which increases the amount or the speed of the cooling action in comparison to natural convective cooling.

Figure 11:
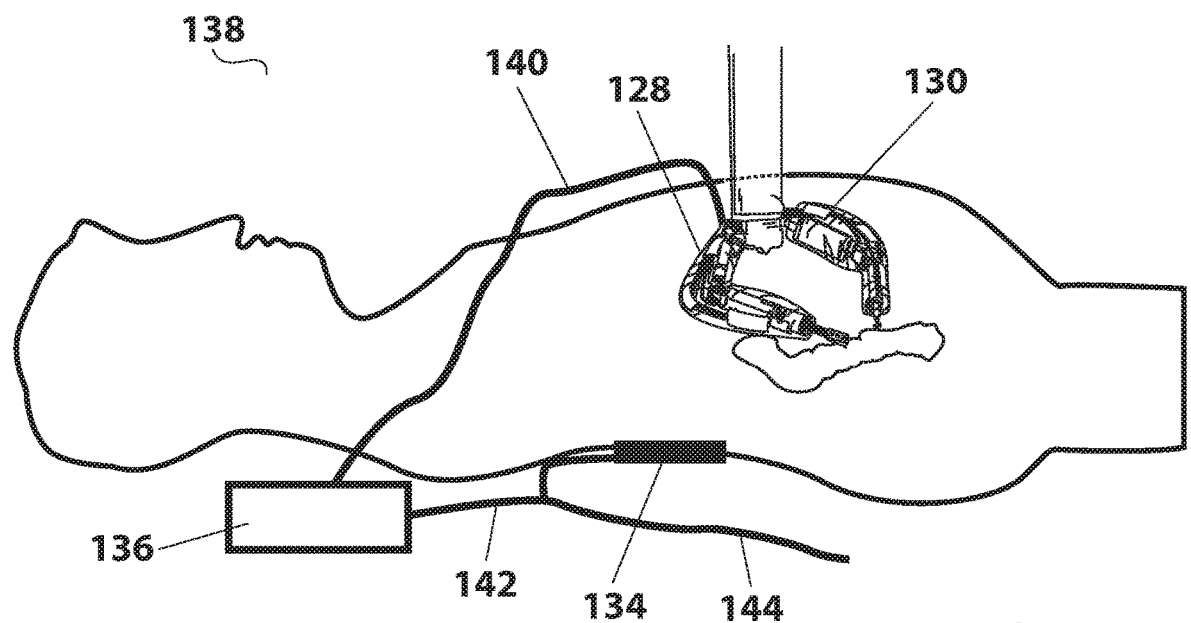
FIG. 11 is a schematic view of a contact detection system, according to one embodiment.

Operation of a robotic device having moveable arms, and especially moveable arms with elbow joints, creates the risk that those arms or the elbows of those arms can contact the patient's cavity wall, potentially causing serious damage to the patient and/or the device. During a procedure, a camera positioned on the device such that it is disposed between two arms has a viewpoint that does not capture the elbows, meaning that the user generally cannot detect or observe any contact between the arms and the cavity wall. One solution is a contact detection system such as the exemplary embodiment depicted in FIG. 10. In this embodiment, a robotic device 120 has a device body 122, two arms 124, 126 coupled to the body 122, and two contact detection sleeves 128, 130 positioned over those arms 124, 126. According to certain embodiments, the sleeves 128, 130 also serve as sterilization sleeves that help to maintain a sterile field for the robot arms 124, 126. In another implementation, as best shown in FIG. 11, the sleeves 128, 130 are part of a contact detection system 138 that is made up of the sleeves 128, 130, a grounding pad 134 attached to the patient's skin, and at least one sensor 136 that is operably coupled to the sleeves 128, 130 and the pad 134. More specifically, the sensor 136 is electrically coupled to the sleeves 128, 130 via a wire 140 that extends from the sleeves 128, 130 to the sensor 136. Further, the sensor 136 is electrically coupled to the pad 134 via wire or elongate member 142 that extends from the sensor 136 to the pad 134. In addition, in one embodiment in which one end effector is a monopolar cautery device, the pad 134 is also electrically coupled to a cautery generator (not shown) via wire or elongate member 144. That is, embodiments having a monopolar cautery device, the device requires a grounding pad (independent of any grounding pad—such as pad 134—for the contact detection system). Thus, in one embodiment, the grounding pad 134 serves as a grounding pad not only for the detection system 138, but also the monopolar cautery device. Alternatively, separate grounding pads are provided for the system 138 and the end effector. It is understood that the wires 140, 142, 144 can also include a cord, an elongate member, or any other electrical connection component.

Figure 12:
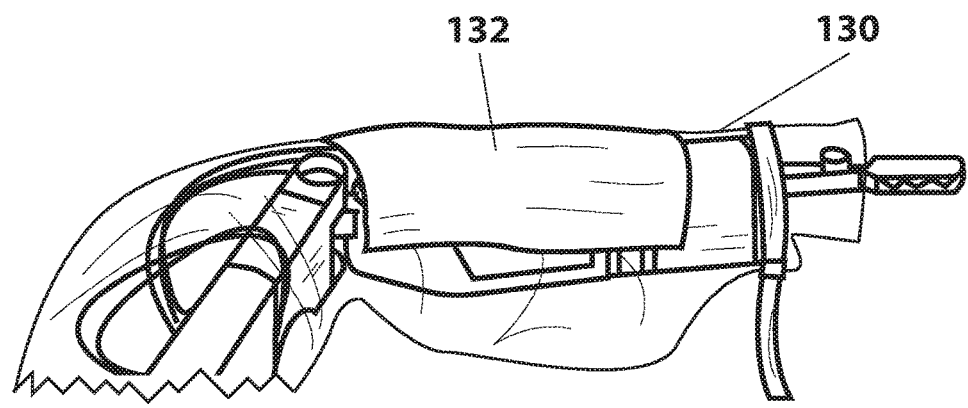
FIG. 12 is a perspective view of a portion of the robotic surgical device of FIG. 10.

According to one embodiment, each of the contact detection sleeves 128, 130 has contact sections (also referred to as "patches") 132 (as best shown in FIG. 10) that are made of a conductive material such as copper and positioned along an external portion of the sleeve 128, 130. For example, a contact section 132 made of copper is schematically depicted in FIG. 12. Alternatively, the material can be silver, aluminum, or gold. In a further alternative, the material can be any known conductive material that could be used in a contact detection system. In one embodiment, the contact sections 132 are copper mesh patches 132. In one implementation as best shown in FIGS. 10 and 12, the patches 132 can be positioned strategically along the sleeves 128, 130 at those areas of the arms 124, 126 that are most likely to make inadvertent contact with an interior wall or other portion of a patient's cavity. For example, as depicted in FIG. 10, there are three patches 132 positioned along an external portion of each sleeve 128, 130, with one patch 132 positioned near each shoulder, one patch 132 at each elbow, and one patch 132 near the distal end of the forearm of each arm 124, 126. In another example, as shown in FIG. 11, the patch 132 is positioned at the elbow of the robotic arm. Alternatively, the patches 132 can be positioned at regular intervals across the exterior of each sleeve 128, 130. Alternatively, the patches 132 are distributed according to any other known pattern or strategy for positioning the patches 132 on the sleeves 128, 130. In a further alternative, the sleeves do not have patches. Instead, the sleeves—such as sleeves 128, 130—could be made up of two or more layers of material that can interact such that the sleeves themselves can detect contact and transmit a signal based on such contact (similar to the way in which a touchscreen works). These patch-less sleeves also eliminate the need for a contact pad.

As shown in FIG. 11, the grounding pad 134, in one embodiment, is positioned on the patient's lower back. The pad 134 is electrically connected to the contact sections 132 via the electrical wire discussed above such that any contact between a contact section 132 and the patient's body (including an internal cavity of the patient) creates a conductive path between the contact section 132 and the grounding pad 134. If an electrical connection is made between the contact section 132 and the grounding pad 134 via such a conductive path as a result of contact between the contact section 132 and the patient's internal cavity, the sensor (or sensors) 136 is triggered, thereby notifying the surgeon or another user that contact has been made between one of the robotic arms and a wall of the patient's cavity. Alternatively, the pad 134 can be positioned anywhere on the patient or in contact with the patient so long as the pad 134 is electrically accessible through all parts of the patient. In one implementation, the grounding pad 134 is a commercially-available grounding pad used in monopolar electrocautery.

One specific embodiment of a contact patch 132 is schematically depicted in FIG. 12. In this embodiment, the sleeve 130 has this single contact patch 132 positioned at or near the elbow of the robotic arm over which the sleeve 130 is positioned. Alternatively, the sleeve 130 can have two or more patches 132 in any of a number of configurations. In various other embodiments, the positioning of the one or more patches 132 can depend on the structure or configuration of the robotic arm (or other portion of the robotic device) or the expected movements thereof.

In use, when one of the arms 124, 126 makes contact with the patient's cavity wall, the sleeve 128, 130 on that arm, and thus at least one of the contact patches 132 on that sleeve 128, 130, makes contact with the cavity wall, thereby completing an electrical circuit running through the patch 132, the grounding pad 134, and the at least one sensor 136 such that the sensor 136 provides a notification to the user about the contact between the arm 124, 126 and the cavity wall. In one embodiment, the extent of the contact can impact the extent of the notification or feedback. That is, the harder the arm 124, 126 contacts the wall or the greater the surface of the arm 124, 126 that contacts the wall, the more the wall deforms and conforms to the shape of the arm 124, 126, thus increasing the amount of surface of the sleeve 128, 130 that contacts the wall. The increased contact surface of the sleeve 128, 130 triggers a stronger electrical connection, and the sensor 136 can be configured to provide a greater or different notification based on the stronger electrical connection. Alternatively, the location of the contact can be provided in the notification or feedback. That is, each patch 132 can be uniquely identified according to any known fashion such that the notification or feedback provides information not only about the contact, but also information about the identity of the patch 132 at which the contact occurred. According to one embodiment, this system can help detect any collision or other contact between an arm and the patient's cavity wall or an internal organ and thus help the user to better control the movements that are made using the robotic device. The sensor's notification of the contact can help to prevent the user from doing further harm to the patient or the robotic device.

In a further embodiment, the sleeves 128, 130 can also be configured to be electronic noise reduction sleeves 128, 130 (also referred to herein as "Faraday sleeves"). More specifically, in certain embodiments, the sleeves 128, 130 are electronic noise reduction sleeves 128, 130 made at least in part of a woven copper mesh. In at least one exemplary implementation, the sleeves 128, 130 are made entirely of a tightly woven mesh made of copper and are grounded. Alternatively, the woven mesh is made of any mesh made of any known conductive material. For example, alternative conductive materials include, but are not limited to, silver, aluminum, and gold. The sleeves 128, 130, in addition to providing a sterilized field for the robotic arms 124, 126, can reduce or terminate the electronic interference (also referred to herein as "noise") created by the multiple different electronic components in the robotic device, including, for example, motors and end effectors such as cautery components.

Another embodiment disclosed herein relates to improved methods and devices for maintaining the sterilization of a robotic device such that the device can be reused. Robotic surgical devices such as the various embodiments disclosed herein are exposed to many different body fluids during a procedure. In order to be able to reuse a surgical device, the device must be fairly impermeable to those fluids. While most components of the various robotic devices disclosed and contemplated herein are positioned such that they generally do not contact any of the body fluids, the end effectors at the distal ends of the robotic arms are, by design, intentionally in contact with or even immersed in the fluids as the end effectors are used to perform a procedure. Typically, mechanical seals such as o-rings can be used to maintain the fluidic seal in the robotic devices contemplated herein. However, o-rings may not work as effectively for certain end effectors.

Figure 13:
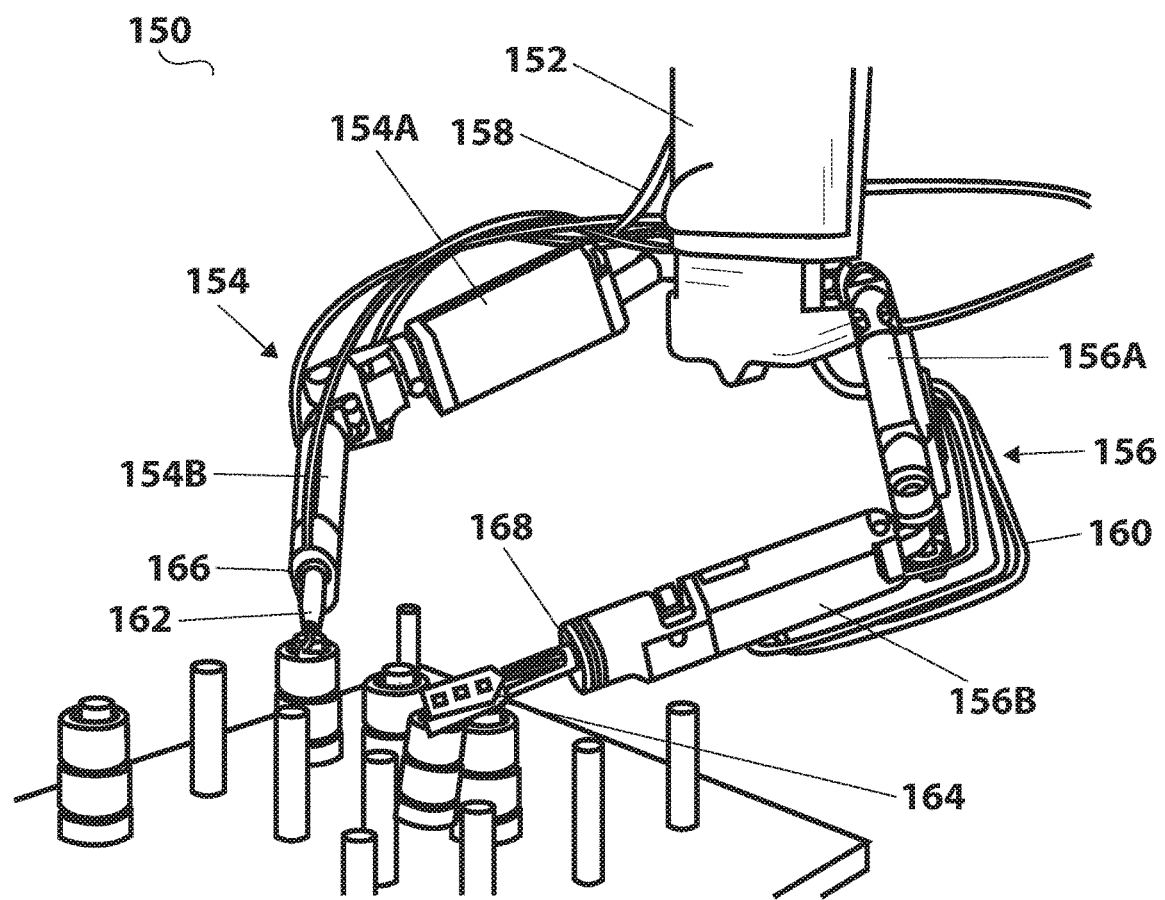
FIG. 13 is a perspective view of robotic surgical device with a pressurization system to maintain a fluidic seal, according to one embodiment.

FIG. 13 depicts one embodiment of a robotic device 150 that uses pressurization to maintain a fluidic seal and thereby maintain the sterilization of the device 150. More specifically, the device 150 has a body 152 and two arms 154, 156 coupled to the body 152. Each of the arms 154, 156 has an upper arm 154A, 156A and a forearm 154B, 156B. In this embodiment, the device 150 also has at least one pressurization tube 158, 160 associated with each arm 154, 156. More specifically, each pressurization tube 158, 160 is operably coupled to a forearm 154B, 156B such that the tube 158, 160 forces pressurized air into an interior portion of the forearm 154B, 156B. It is understood that the term "tube" as used herein is intended to mean any tube, pipe, line, or any other known elongate member having a lumen that can be used to deliver pressurized air. In this embodiment, the interior portion of each forearm 154B, 156B is fluidically sealed in relation to the air outside the forearms 154B, 156B except for the distal opening 166, 168 in the forearm 154B, 156B from which the end effector 162, 164 extends. In accordance with one implementation, the pressurization tubes 158, 160 force pressurized air into the forearms 154B, 156B such that their interior portions have pressures that are higher than the air pressure inside the patient's cavity, thereby creating a constant flow of air out of the forearms 154B, 156B through the distal openings 166, 168.

In use, the pressurization tubes 158, 160 pressurize the interior portions of the forearms 154B, 156B such that there is a constant flow of pressurized air out of the distal openings 166, 168 of the forearms 154B, 156B. This constant flow from each forearm 154B, 156B operates based on the same principle as a clean room—the flow of air maintains the sterility of the interior portions of the forearms 154B, 156B by preventing the fluids from accessing those interior portions. That is, the constant flow of air keeps any liquids outside the forearms 154B, 156B from entering through those distal holes 166, 168.

Figure 14A:
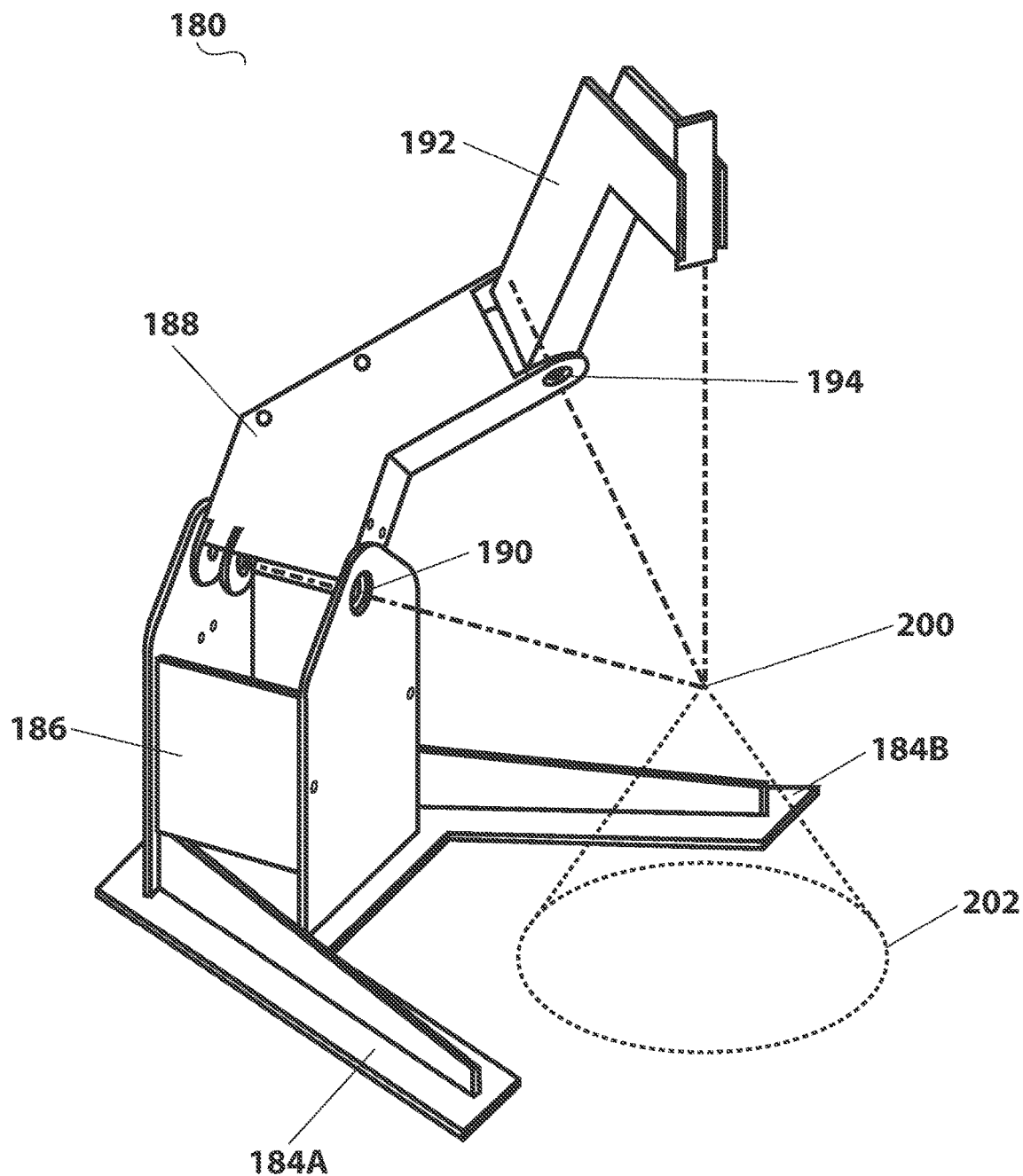
FIG. 14A is a perspective view of an external gross positioning system, according to one embodiment.
Figure 14B:
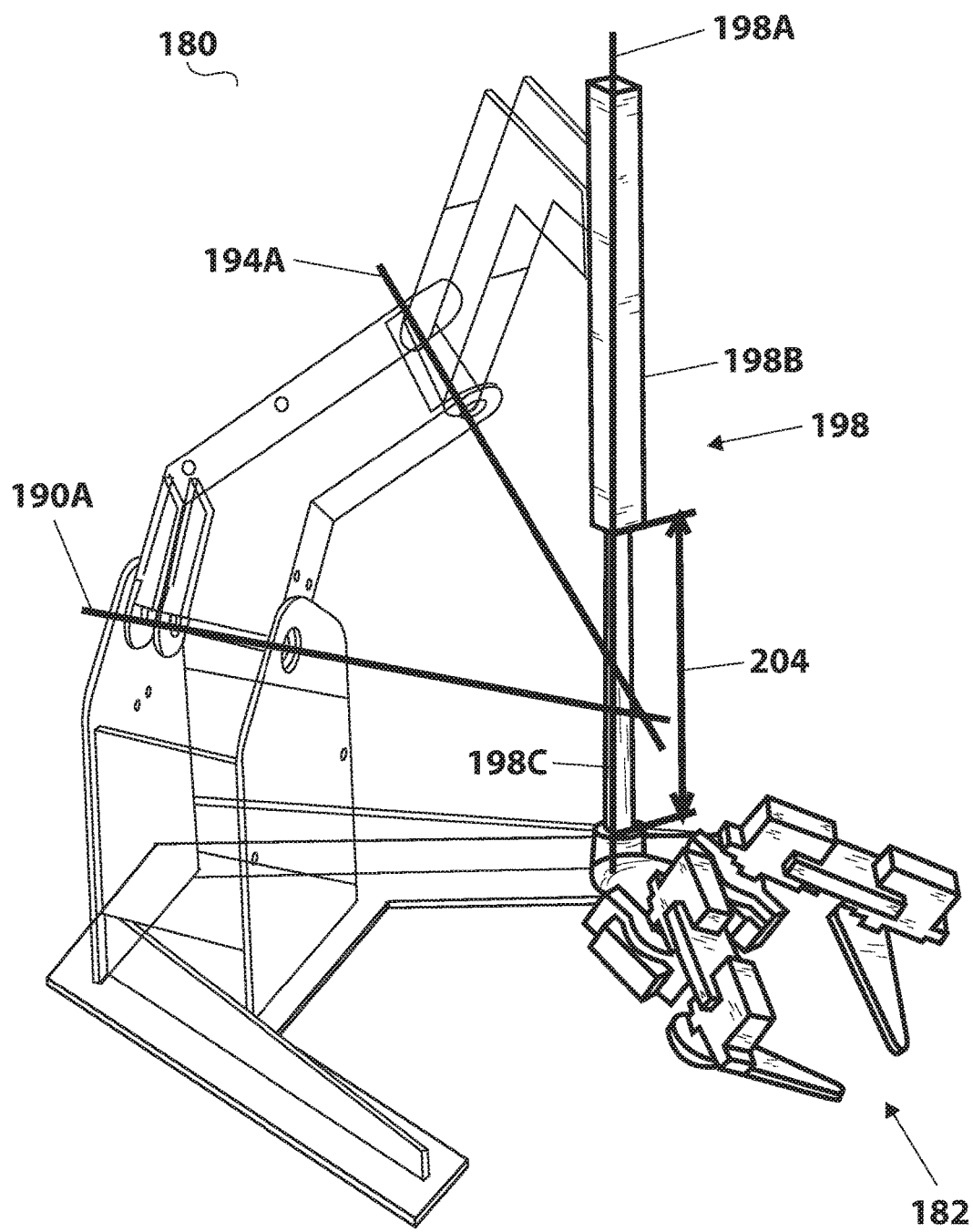
FIG. 14B is a further perspective view of the external gross positioning system of FIG. 14A.

FIGS. 14A and 14B depicts an external gross positioning device and system 180 that can be used to automatically grossly position a surgical device 182 inside a cavity of a patient (as best shown in FIG. 14B, according to one embodiment. "Gross positioning," as used herein, is intended to mean general positioning of an entire moveable surgical device (in contrast to precise placement of the specific components of such a device, such as an arm or end effector). In known robotic surgical systems, the positioning of those devices during a surgical procedure can be a challenging task. Further, minimally invasive surgical procedures (using either robotic or non-robotic systems) frequently require a surgical technician to reposition the surgical equipment, such as a laparoscope. Such repositioning takes time and additional effort. In addition, in some cases, the surgical technician is a junior medical student who is not fully trained in laparoscopy. As a result, the repositioning instructions from the surgeon often result in an obstructed and/or fogged view of the surgical site, requiring additional cognitive resources from the surgeon. Hence, the Da Vinci® system and known single incision surgical devices often require timely repositioning of the patient, the robotic system, or both while performing complicated procedures.

The various gross positioning devices contemplated herein aid in the repositioning of surgical devices (including, for example, any surgical devices that have a device body or rod configured to be positioned through an incision and at least one robotic arm coupled to the device body that is positioned entirely within the cavity of the patient) throughout the procedure without additional intervention from the surgical staff. The gross positioning system embodiments are capable of controlling the degrees of freedom, azimuth and elevation angle, and roll and translation about the axis of insertion of laparascopic surgical tools, including robotic laparoscopic surgical tools. As a result, the gross positioning device embodiments disclosed and contemplated herein can grossly position a surgical device through an incision into a patient cavity such as the abdominal cavity with high manipulability, reducing the operative time and stress induced upon the surgical staff. The combination of the external gross positioning system with the internal surgical device system will allow the degrees of freedom of the internal system to effectively increase without increasing the size of the surgical robot/device.

In one implementation, the various devices described and contemplated herein can be used with any single site surgical device with an available external positioning fixture, such as a protruding rod or magnetic handle.

This system embodiment 180 has a base 184 and a body 186 coupled to the base. An upper arm or first arm link 188 is rotatably coupled to the body 186 at a rotational coupling or joint 190 such that the upper arm 188 can rotate in relation to the body 186 around the axis 190A as best shown in FIG. 14B. A forearm or second arm link 192 is rotatably coupled to the upper arm 188 at a rotational coupling or joint 194 such that the forearm 192 can rotate in relation to the upper arm 188 around the axis 194A as best shown in FIG. 14B. The device 180 also has a third link or extender 198 (best shown in FIG. 14B) coupled to the forearm 192. The extender 198, according to one embodiment, has two degrees of freedom: it can both rotate and extend laterally. That is, the extender 198 is configured to move between an extended position and a retracted position and any position in between. In one embodiment, the amount of extension and retraction is depicted by the arrow 204 in FIG. 14B. As shown in FIG. 14B, the extender 198 can have two components: a stationary body 198B and an extendable rod 198C. In this embodiment, the extendable rod 198C extends from and retracts into the stationary body 198B as shown. Further, the extender 198 can also rotate around axis 198A. More specifically, in the depicted embodiment, the body 198B and the extendable rod 198C are rotationally coupled to each other such that they both rotate around axis 198A together. Alternatively, the extendable rod 198C can rotate in relation to the stationary body 198B around axis 198A while the stationary body 198B does not rotate. Alternatively, the extender 198 can be any known component or device that provides both extension and rotation as contemplated herein.

Figure 15:
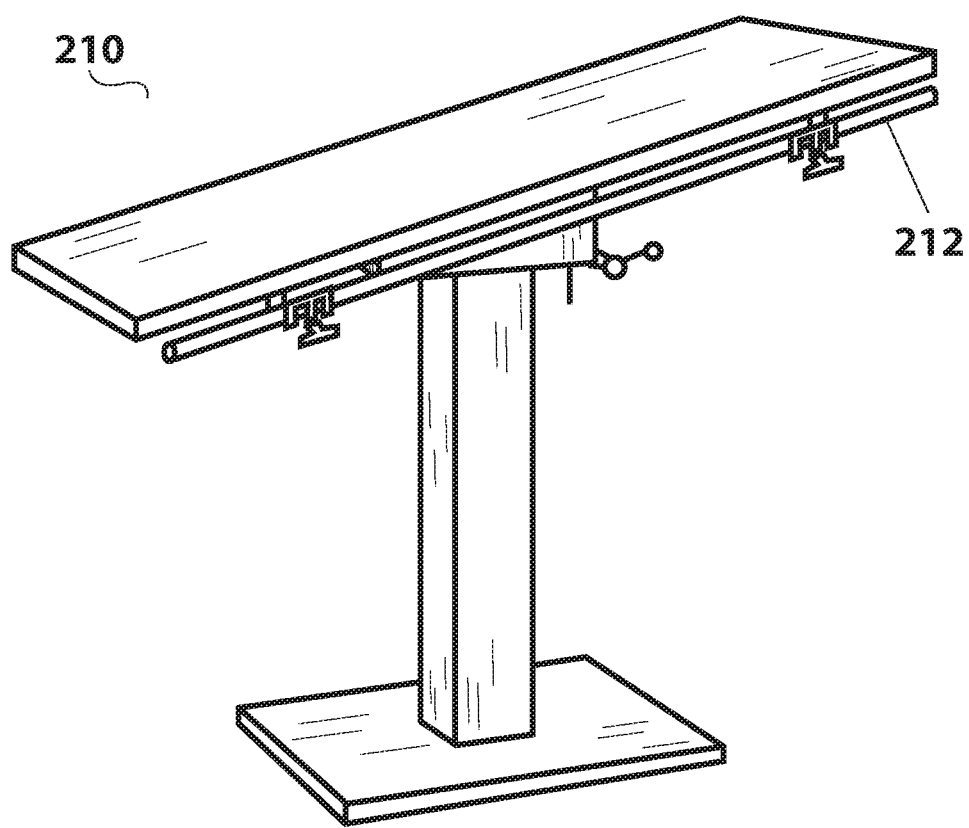
FIG. 15 is a perspective view of a standard surgical table.

In one implementation, the base 184 is configured to keep the entire device 180 stable and secure during use. As shown, the base 184 is made up of two extended pieces or "feet" 184A, 184B (best shown in FIG. 14A) that provide stability and help to prevent the device 180 from tilting or tipping during use. In alternative embodiments, the base 184 can be any structure that provides such stability, including, for example, a very heavy or weighted structure that uses the weight to enhance stability. In certain implementations, the base can be stably coupled to a surgical table on which the patient is placed, such as the known surgical table 210 depicted in FIG. 15. According to one implementation, the base 184 can be coupled to a rail 212 on the table 210. In a further alternative, the base 184 can be coupled to any fixed object in the operating room. Alternatively, the base 184 can be coupled to or be an integral part of a cart or other mobile standalone unit.

In one embodiment, the rotational axis 190A at rotational joint 190 (between the body 186 and the upper arm 188) is perpendicular to both the rotational axis 194A at rotational joint 194 (between the upper arm 188 and the forearm 192) and the rotational axis 198A. In other words, each axis 190A, 194A, 198A can be perpendicular in relation to the other two. The three axes 190A, 194A, 198A being perpendicular can, in some implementations, simplify the control of the system 180 by causing each axis 190A, 194A, 198A to contribute solely to a single degree of freedom. For example, if the extender 198 is rotated around axis 198A, the tilt of the surgical device 182 does not change when all three axes 190A, 194A, 198A are perpendicular. Similarly, if the upper arm 188 is rotated around axis 190A, only the tilt of the surgical device 182 from side to side is affected. Alternatively, two of the three axes 190A, 194A, 198A are perpendicular to each other. In a further alternative, none of the axes 190A, 194A, 198A are perpendicular to each other.

In one embodiment, the three axes 190A, 194A, 198A (as best shown in FIG. 14A) intersect at the intersection 200 (as best shown in FIG. 14B), also known as a "spherical joint" 200. The intersection 200 remains fixed at the same location, regardless of the positioning of the arm links 188, 192, 198, and can be used as the insertion point during surgeries. In one implementation, the intersection 200 causes the system 180 to act similarly to a spherical mechanism. A "spherical mechanism" is a physical mechanism or software application that can cause all end effector motions to pass through a single point, thereby allowing a surgical system to use long rigid tools that perform procedures through incisions that serve as single pivot points. As an example, both COBRA-Surge and the Raven have mechanical spherical mechanisms, while Da Vinci has a software-based spherical mechanism. In the device 180 as shown in FIG. 14A, the configuration of the device 180 creates the spherical joint 200 such that the extender 198 must pass through the single point of the spherical joint 200. The spherical joint 200 created by the device 180 increases the size of the effective workspace (depicted by the cone 202) for the surgical device 182.'

Alternatively, the gross positioning device 180 can have a fourth link, a fifth link, or any number of additional links, and a related additional number of rotational joints. Further, the device 80 can also have fewer than three links, and a related number of rotational joints. Thus, in one specific alternative implementation, the device 180 can have solely a base (such as base 184), a body (such as body 186), and a first link (such as first link 188) with a single rotational joint (such as rotational joint 190). In sum, the gross positioning device 180 can have a single rotational joint, two rotational joints, or any number of rotational joints.

In use of the embodiment shown in FIGS. 14A and 14B, the arm links 188, 192, 198 rotate about axes 190A, 194A, 198A to position the surgical device 182 within the surgical space defined by the cone 202. The cone 202 is a schematic representation of the outer boundaries of the space in which the device 182 can be positioned by the positioning device 180. More specifically, the extender 198 can be rotated around axis 198A to rotate the surgical device 182 about the axis 198A. Further, the arm links 188, 192 in combination with the extender 198 can be used to articulate the device 182 through two separate angular planes. That is, the two axes 190A and 194A can affect the angular position of the extender 198. In addition, the extender 198 can be extended or retracted to allow for the surgical device 182 to be advanced into and out of the patient's body cavity.

In one implementation, the positioning system 180 and the surgical device 182 (as shown in FIG. 14B) can be used in combination, such that the surgical device 182 is treated as an extension of the positioning system 180 wherein both are used together to move and operate the surgical device 182. For example, the surgeon may want to move the surgical device 182 a total of one inch to the right and thus actuates an external controller to cause this move. The controller transmits the appropriate signals to the system 180 and the surgical device 182 such that the system 180 and device 182 work in combination to move the surgical device 182 one inch to the right. In one example, the system 180 could move 0.5 inches and the device 182 could move 0.5 inches, thereby resulting in the device 182 moving the full one inch as desired. According to one embodiment, the system 180 can thus be used to maximize the strength, workspace, and maneuverability of the combination of the system 180 and the device 182 by determining the optimal contribution of each component during use.

Alternatively, the system 180 and the device 182 operate separately. That is, the system 180 is not operable or does not operate while the device 182 is being used, and the device 182 is not operable or does not operate while the system 180 is being used. For example, if the device 182 is being used and it is determined that a target object in the surgical space is outside the reach of the device 182, the device 182 is "shut down," otherwise rendered inoperable, or simply placed in a "pause mode," and the system 180 is used to reposition the device 182 accordingly.

It is understood that the device 180 can be operably coupled to a processor or computer (not shown) such that the processor can be used to control the system 180, including movement of the arm links 188, 192, 198 to grossly position the surgical device 182.

In alternative embodiments, the system 180 can have an arm that has only 2 arm links, or in yet another alternative the arm can have only 1 arm link.

In a further alternative implementation, the system 180 can also be configured to incorporate or integrate equipment or devices that couple to the surgical device 182 to provide various functionalities to the device 182. For example, in one embodiment, the positioning device 180 can contain suction and irrigation equipment that couples to corresponding equipment in the surgical device 182 such that the surgical device 182 includes suction and irrigation components. In another example according to a further implementation, the positioning device 180 can contain any known equipment that is configured to couple to corresponding equipment in the surgical device 182.

Alternative embodiments contemplated herein also include systems that can be used with surgical devices that are magnetically controlled (in contrast to the surgical device depicted in FIGS. 14A and 14B, which is controlled via a positioning rod inserted through the surgical incision). In those implementations, the positioning system positions the surgical device anywhere along an internal surface inside the patient's cavity by positioning an external magnetic component (such as a magnetic handle or other type of external magnetic component) along the outer skin of the patient. This positioning of the device can include any combination of movement in two dimensions along the surface of the patient's skin as well as rotation of the external magnetic component about an axis perpendicular to the surface of the skin. Of course, it is understood that while the movement of the magnetic component along the skin of the patient is considered to be two dimensional, the patient's skin is curved such that movement of the external component along the skin demonstrates absolute manipulation in all six degrees of freedom.

Figure 16A:
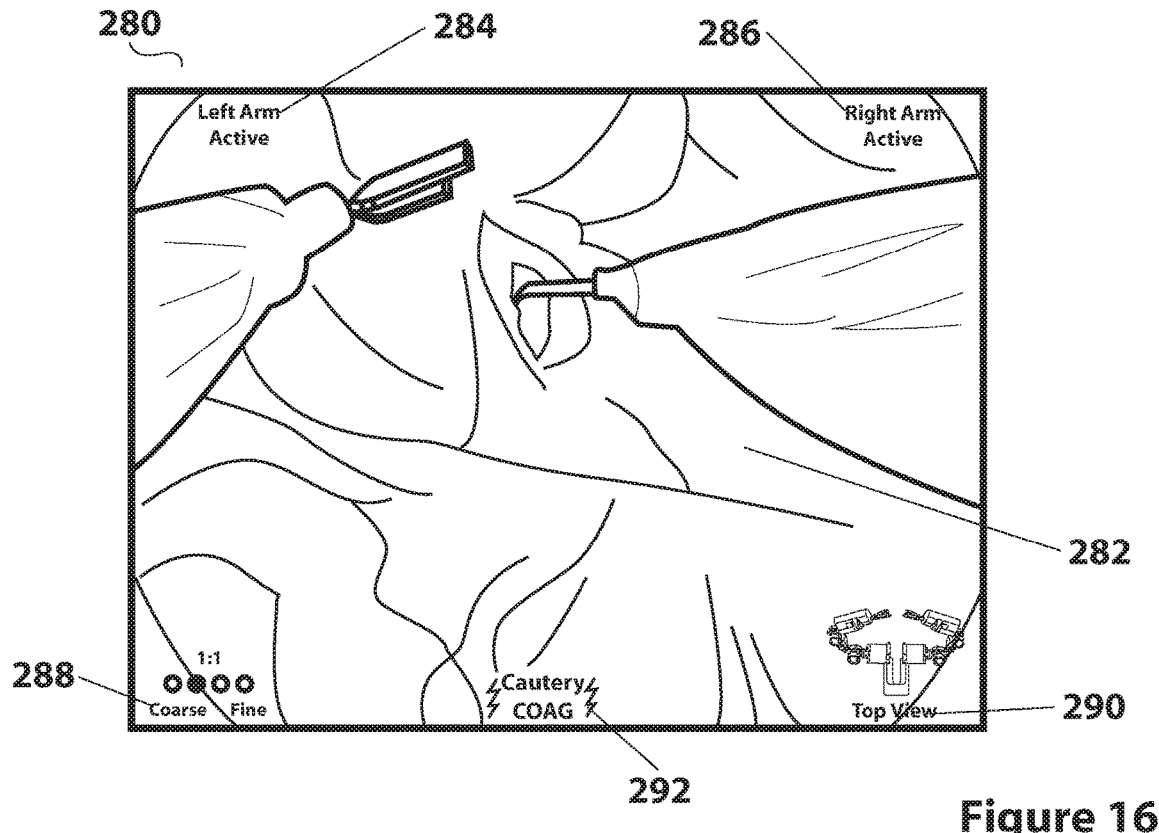
FIG. 16A is a schematic depiction of a user interface for a robotic surgical system, according to one embodiment.

Another set of embodiments disclosed herein relates to a user interface and related software applications for use in surgical robotics. FIG. 16A depicts a user interface 280, according to one embodiment. The interface 280 provides a visual display 282 of the surgical space as captured by a camera. In addition, the interface 280 can also provide additional information via various icons or informational overlays positioned on the interface 280 in any configuration chosen by the user. For example, in the user interface 280 depicted in FIG. 16A, the left arm status overlay 284 is positioned in the upper left hand corner of the interface 280, while the right arm status overlay 286 is positioned in the upper right hand corner. Further, the device controller sensitivity overlay 288 is positioned in the lower left hand corner, and the device configuration overlay 290 is positioned in the lower right hand corner. In addition, the cautery status overlay 292 is positioned in a middle portion of the lower edge of the display 282. The interface 280, according to one embodiment, is fully customizable such that the user (typically a surgeon) can actively arrange the icons or overlays on the display 282 in any configuration that the user desires. In an alternative embodiment, all of the informational overlays can be positioned along one edge of the display 282.

Figure 16B:
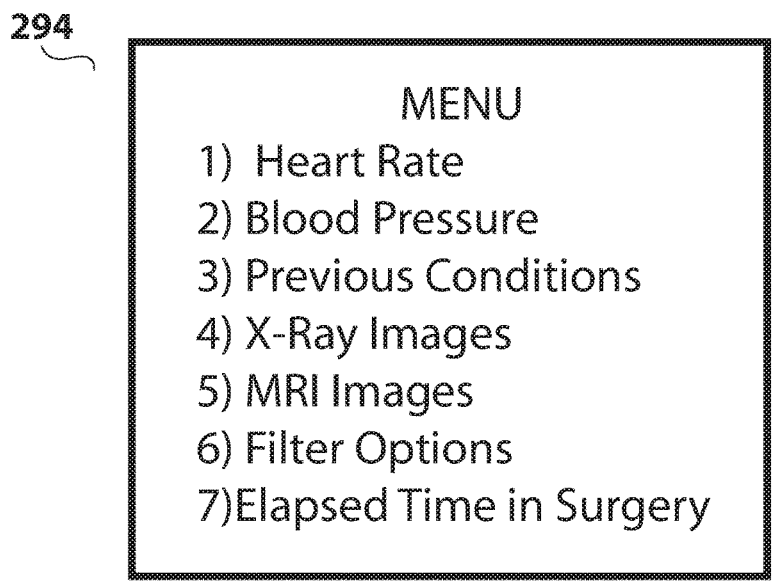
FIG. 16B is a schematic depiction of a menu that can be displayed on the user interface of FIG. 16A.

In another implementation, the interface 280 can be triggered to display a menu, such as, for example, the menu 294 as shown in FIG. 16B. According to one embodiment, the menu 294 can display and provide access to various types of additional information. The menu 294 can be triggered by actuation of a button (not shown) that both freezes the robotic device and causes the display of the menu 294. Alternatively, the button can simply cause the display of the menu 294. In one exemplary embodiment as shown in FIG. 16B, the additional information on the menu 294 includes real-time patient information such as the patient's current heart rate and blood pressure. Further, the menu 294 can also provide access to historical patient information such as previous conditions, X-ray images, and MRI images of the patient. In addition, the menu 294 can also provide additional information about the current surgical procedure, such as the elapsed time in surgery. Further, the menu 294 can provide any other relevant or useful realtime or historical information.

In use, before a surgical procedure begins, the surgeon can position different informational overlays or icons on the display 282 as the surgeon desires. Further, the user can actuate a button on the user interface 280 or operably coupled thereto at any time before, during, or after a procedure to trigger the display of the menu 294. For example, the surgeon might notice something strange or unexpected during a procedure and actuate the button to display the menu 294 in order to access the patient's current heart rate or blood pressure, for example. Alternatively, the surgeon might want to select a different camera filter or different lighting during a procedure to better visualize certain structures or areas of the surgical space. According to one embodiment, the user interface 280 can act as an informational hub for decision-making during the procedure and/or during emergencies that might occur during the procedure. The user interface 280 provides enhanced surgeon comfort and ergonomics in comparison to known consoles and interfaces for robotic surgical systems by allowing for easy real-time adjustments to the display 282 to fit the needs of the surgeon, technician, or other user.

In a further implementation, a display 282 accessible to and used by multiple users over time (such as on a surgical system in an operating room in a hospital) can be configured to be quickly and easily set to the personalized settings of a specific user. That is, a specific user can configure the display 282 as desired at any time, including the placement of the informational overlays and other configurable settings of the display 282. That configuration of the display 282 can be saved and associated with the user's profile or account such that the user can access the configuration whenever the user accesses her or his account while using the interface 280. In one embodiment, the interface 280 allows for the saving of and access to the user personalized settings through a personalized login in which each user must log in to the interface 280 system each time the user wants to use it.

Figure 17:
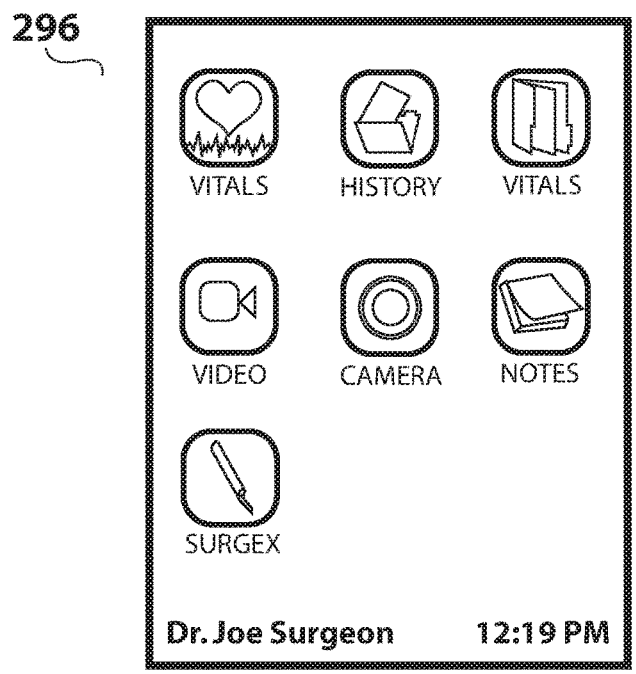
FIG. 17 is a schematic depiction of a personalized display for a robotic surgical system, according to one embodiment.

For example, the interface 280 can require a specific username and password for each user such that each time the user first interacts with the interface 280, the display 282 launches a screen or overlay that prompts the user to enter a username and password or any other type of personalized login information. Only after the user enters the correct personalized login information is the interface 280 triggered to provide access to the user and further to configure the display 282 as previously configured by the user. One example of a personalized configuration of a display 296 is shown in FIG. 17 for exemplary purposes only. Alternatively, the interface 280 can be operably coupled to a card reader (not shown) such as an RFID or NFC reader such that the user must swipe a personalized ID badge or card near or through the card reader in order to access the interface 280. In a further alternative, the interface 280 can be operably coupled to another type of scanner, such as a facial recognition or biometric (such as fingerprint, iris, etc.) scanner such that the user must first use the scanner in order to access the interface.

Another set of embodiments disclosed herein relates to software applications to provide feedback to a user relating to her/his surgical performance. The software applications can be used with a user interface such as, for example, the user interface embodiments described above, or alternatively any processor or computer. Certain embodiments compare performance parameters to standard benchmark performance parameters, while other embodiments track performance parameters over time.

In one embodiment, a software application is provided to track and compare surgical tool endpoint positions. It is understood that during a procedure, the surgical tool endpoint positions are indicative of the skill level of the surgeon. That is, an experienced surgeon will operate the surgical tool with control and very little wasted motion. In contrast, a novice will operate the tool with less control and more wasted motion. Similarly, the total distance traveled by a surgical tool endpoint can also be indicative of skill level. The shorter the distance, the more experienced the surgeon.

Figure 18:
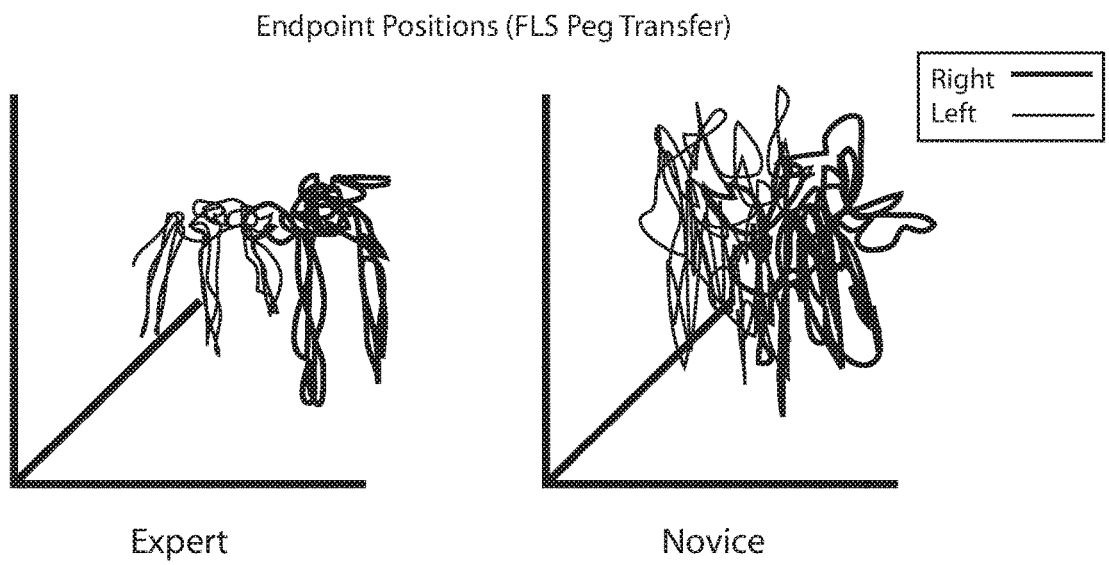
FIG. 18 shows two graphs showing the endpoint positions of robotic surgical tools operated by two different surgeons, wherein the endpoint positions were tracked during a peg transfer test.

According to one implementation, the software application tracks the tool endpoints and plots those tracks in a graph. For example, FIG. 18 depicts two different graphs of endpoint positions tracked during an FLS peg transfer test—the left graph depicts the endpoint track of an experienced surgeon, while the right graph depicts the endpoint track of a novice surgeon. Thus, such a graphical display qualitatively shows the experience or skill level of a surgeon. Alternatively, the software application can track the tool endpoints and report information about the total distance traveled or the total enclosed volume. In accordance with one implementation, the software application can collect the information over time, thereby allowing for tracking of a surgeon's progress from a novice to a more experienced surgeon or to an expert.

In another embodiment, the software application records and tracks any forces, velocities, and/or accelerations of any components of the surgical tools. It is understood that very careful application of forces and use of smooth motions need to be used during a surgical procedure due to the enclosed and delicate nature of the operating site. In accordance with one implementation, the software application can be configured to limit the force, velocity, or acceleration of any device component during a procedure, thereby preventing the device from exceeding any pre-established limits for those parameters. In a further embodiment or in combination with the parameter limits, the software application can also collect and record the parameter information and make it available at a later time (such as post-surgery, for example), in some cases in combination with the surgical video, to identify any specific instances in which excess motion or force was used. Further, an overall smoothness factor could be calculated by the software application using some combination of the parameters.

One embodiment of the software application utilizes any of the previous parameters to provide benchmark testing for surgeons. The parameter data can be used to compare a surgeon's skills or the skills of groups of surgeons to other surgeons across the country or world. Alternatively, the software application can be used to test any individual surgeon against a known benchmark standard. In a further alternative, yearly or quarterly competency testing could be performed using the software application to certify that the surgeon meets or exceeds the set standard.

In addition to benchmark testing, in one embodiment the same information can be used by the software application to monitor the state of a surgeon or user during a procedure. As an example, the system can measure any tremor by the surgeon during the procedure and compare it to the surgeon's normal state as established based on information collected during past actual procedures or practice procedures.

In another software application embodiment relating to feedback, the software is configured to provide warm-up or practice exercises for a surgeon, including providing such exercises just prior to performing an actual surgery. It has been shown that "warming up" prior to a surgical procedure improves the performance of a surgeon. In one embodiment, the user console contains the software application and the application provides a virtual reality environment for the user using the user console. The application can provide an example procedure in a virtual reality environment for the surgeon to perform that is similar to the actual procedure. Alternatively, the application can provide specially designed warm-up tasks, procedures, "games," or any other type of warm-up activity for the surgeon to perform prior to the actual procedure.

It should be noted that any of the software application embodiments relating to feedback as described herein can be operated on any known operating system. For example, the software application can be used with any known user interface for a surgical system, any known controller for any surgical system, or any known processor or computer system. In certain embodiments, a surgical device can be coupled to the user interface or the computer, or alternatively, the user interface or computer can be used by the user to operate the software application without a surgical device coupled thereto. In yet another alternative, a surgeon at a remote training center could use a computer, controller, or user interface that is linked to a robotic trainer or other type of training system at a central location to interface with the software application and perform tasks such as tests or warm-up procedures.

It should also be noted that the data relating to the various parameters discussed above can be collected using sensors coupled to the surgical tools. Alternatively, the data can be provided by the controller based on information already available from the controller. In a further embodiment, the data can be collected in any known fashion using any known devices.

Another set of embodiments disclosed herein relates to controllers or consoles for use with various surgical systems, including robotic surgical systems.

Figure 19:
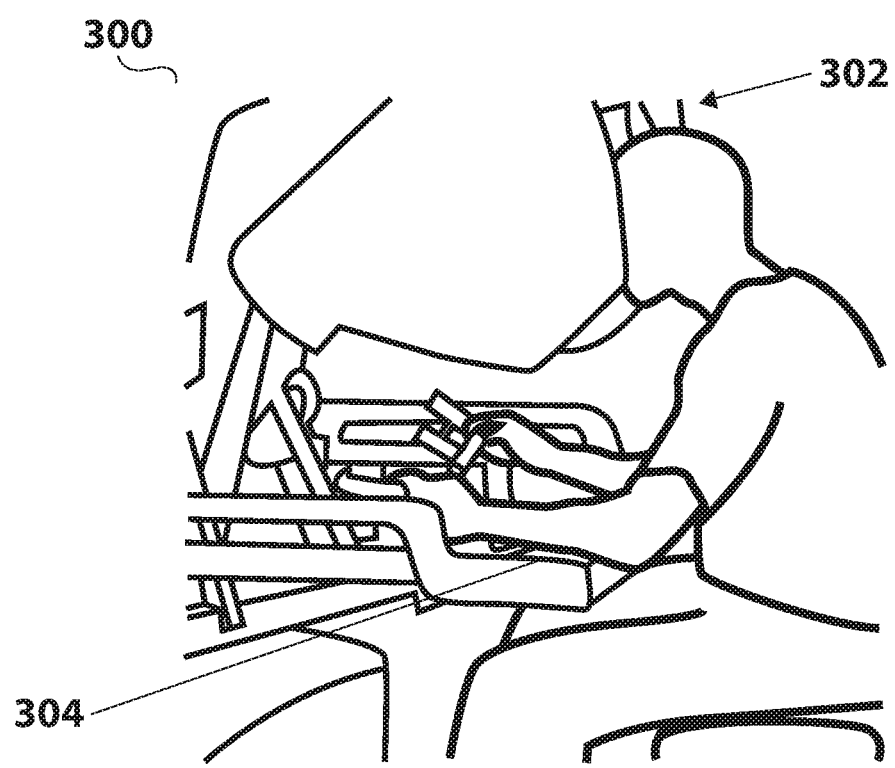
FIG. 19 is a perspective view of a console having at least one biometric sensor, according to one embodiment.

Certain controller or console implementations are configured to collect biometric information relating to the user, including during use of the system for surgery or training. For example, in one embodiment as shown in FIG. 19, a console 300 is provided that is a known Da Vinci™ console or a similar controller. Alternatively, the console 300 can be any known controller that can be used by a surgeon to operate a surgical device and that requires physical contact between the controller and the surgeon. As shown, the console 300 has a viewer 302 that requires the user (such as a surgeon) to place her or his head within the viewer 302 in order to operate the console 300. This results in the head of the user coming into contact with the viewer 302. Similarly, the console 300 has an armrest 304 that allows the user to rest her or his arms while using the console 300. Like the viewer 302, the placement of the armrest 304 results in the user's arms coming into contact with the armrest 304. In this implementation, the console 300 is provided with a sensor or sensors (not shown) associated with the viewer 302 and separately a sensor or sensors (not shown) associated with the armrest 304. The viewer sensor is configured to be in contact with the user's head when the user has correctly placed her/his head within the viewer 302, while the armrest sensor is configured to be in contact with the user's arm or arms when the user rests her/his arm or arms on the armrest 304. These sensors can be configured to collect various biometric information regarding the user, such as, for example, temperature, breathing patterns, pupil dilation, blinking (excessive blinking can indicate irritation or tiredness), muscle tension, and/or pulse rate. Alternatively, any other biometric information that can be indicative of a user's physical state can be detected and/or collected. According to one embodiment, these metrics can be collected by the sensors and used to track the user's physical state during a procedure.

According to one implementation, the information about the user's physical state can be used to modify the operation of the surgical system. For example, in one implementation, any biometric information indicating excessive stress or anger or the like can trigger the system to automatically minimize, reduce, or shut down the movement of the components of the surgical device. That is, any predetermined biometric parameter that exceeds a certain predetermined level can cause the processor to trigger the actuators on the surgical device to move at a reduced speed, thereby slowing the movement of the device and reducing the risk of injury to the patient. Further, if the biometric parameter exceeds a second, higher predetermined level, the processor triggers the actuators to stop entirely for a predetermined period, thereby forcing the user to take a short break from the procedure. Alternatively, at this higher level, the processor can be triggered to disconnect the controls from the device for a predetermined period, thereby producing the same result of forcing the user to take a short break.

In accordance with certain alternative embodiments, the console 300 can be linked to a robotic trainer or other type of training system to interface with a software application similar to one of the applications described above, thereby allowing a user to perform tasks such as tests, warm-up procedures, or surgical simulations while the console 300 collects biometric information as described above, thereby allowing for evaluation of the physical state of the user during the simulation or task.

Figure 20:
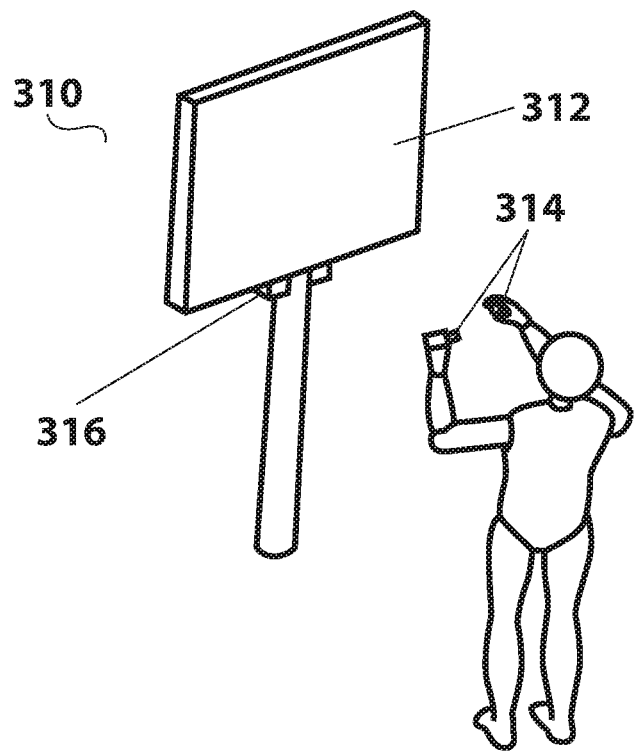
FIG. 20 is a perspective view of a controller for a robotic surgical system, according to another embodiment.

In another controller embodiment as shown in FIG. 20, a controller system 310 is provided that is an open air controller system 310. As used herein, "open air controller" means a controller that allows a user to control a device or system via movement of the user's arms, legs, and body by taking a significant amount of position and orientation measurements via non-mechanical means. Commercial examples of open air controllers include the Wii and XBox Kinect gaming systems. The controller system 310 depicted in FIG. 20 has a monitor 312 configured to display a live video image of the surgical space as captured by one or more cameras associated with the surgical device being used in the procedure. Alternatively, instead of the monitor 312, the system 310 could have a "heads up" display (not shown) that is worn on the head of the user.

The system 310 also has at least one of the following: one or more handles 314 to be held and manipulated by the user and/or a tracking device 316 coupled with or positioned near the monitor 312. For system 310 embodiments having one or more handles 314, the handles 314 can be used to control the surgical device, including the position and orientation of one or more end effectors on the device. These handles 314 work as an electronic means of sensing position and orientation via wireless positioning, accelerometers, gyros, and/or compasses. A commercial example of such a handle is the Wii controller. In one implementation, the handles 314 work in conjunction with the tracking device 316 to control the surgical device using handle tracking in which the tracking device 316 is configured to track identifiable markers associated with each handle 314 and thereby be capable of tracking the position and orientation of each handle 314 and use that information to control the surgical device.

According to one implementation, the handle or handles 314 can also have additional components or features incorporated therein. For example, one handle 314 embodiment can have at least one button or other input component that can be used to allow the user to interact with the system via menus displayed on the monitor 312 or in any other fashion in which the user can communicate with the system via an input component. In one embodiment, the input component can be a button, a scroll wheel, a knob, or any other such component. Alternatively, the handle 314 can have a sensor or any other type of detection component. In use, the user could use the input component or detection component to provide fine adjustments to the system or otherwise communicate with the system as desired or needed.

Alternatively, the system has a tracking device 316 and no handles. In such an embodiment, the tracking device 316 tracks the location and movement of the user's arms and/or hands in a fashion similar to the tracking of the handles as described above, but without the use of any identifiable markers. Instead, the tracking device 316 uses the arms, hands, or other relevant body parts as natural markers. In one implementation, the tracking device 316 is a camera that can be used to identify and track the user or at least the hands and/or arms of the user. According to one embodiment, the tracking device 316 can fully map the user's body such that positional information about various parts of the user's body could be used to control a surgical device. For example, the positional information about the user's elbows might be used to control the surgical device. One commercial example of such a tracking device is the Kinect system used with the XBox gaming system.

Another similar embodiment relates to a tracking device 316 used in conjunction with a cuff or other type of device that is positioned around at least a portion of the user's forearm. The cuff is configured to detect and measure the firing of muscles in the forearm, such that the system can identify hand gestures. Other similar devices for directly measuring of muscle actions that are coupled to other parts of the user's body can also be used with the current system.

In another alternative embodiment, the system 310 is scaled to a smaller size such that the system 310 tracks a user's hands or fingers instead of the user's arms or larger body parts. By tracking the user's hands, very fine motions can be used to control the surgical device. Such a system would reduce the risk of fatigue.

In use, a user or surgeon can stand or sit or otherwise position herself or himself in front of the monitor 312 so that the user can see the surgical space as displayed on the monitor 312, including at least a portion of the surgical device. The user can then use either handles 314 or the user's own arms and/or hands to make motions that will be detected by the system 310 and utilized to control the movements of the surgical device.

A similar embodiment relates to a system configured to control a surgical device based at least in part on eye motion. That is, a motion sensor or monitor—perhaps similar or identical to one of the tracking device embodiments described above—is positioned to track the motion of a user's eye, and that motion can be utilized to control a surgical device. In one implementation, eye motion tracking could help the system recognize the intended tooltip position by tracking where the user is looking.

Another controller embodiment relates to controller (not shown) configured to monitor brainwaves and thereby control a surgical device based on those brainwaves. In one specific embodiment, the controller has an electroencephalography (EEG) sensor that is positioned against or adjacent to the user's head. The EEG sensor senses electrical activity along the scalp of the user and can be used to detect and thereby interpret the brain waves of the user and use that information to control the surgical device. In one implementation, such a system eliminates the need for precise motor skills and relies instead on the user's thoughts to actuate the surgical device.

In a further alternative, the EEG sensor could be used to monitor a user's mental state and work in combination with the system to react to the information about the user's mental state in a fashion similar to that described above with respect to monitoring a user's physical state.

In a further embodiment, the controller has a microphone that detects voice commands and the controller uses those commands to control the surgical device. That is, the user can state verbal instructions that the controller detects via the microphone, and the software in the controller can be configured to analyze what the user said and trigger the device to take the action instructed. One commercial embodiment of a similar system is the Siri system used in Apple products. In use, the user could use voice commands instead of physical manipulation to control a surgical device. In one specific example, surgeons are often required to stop use of one component or device during a procedure to switch to a different task. With this system, the surgeon could verbally instruct the system to switch to the other task.

Another controller embodiment relates to various controller devices having a foot controller. Some prior art controllers have foot controllers made up of multiple foot pedals that require a user to use each foot for more than one function and/or actuate more than one pedal. The foot controller embodiments herein are configured to reduce the functions, make those functions easier, or eliminate the multiple pedals.

Figure 21:
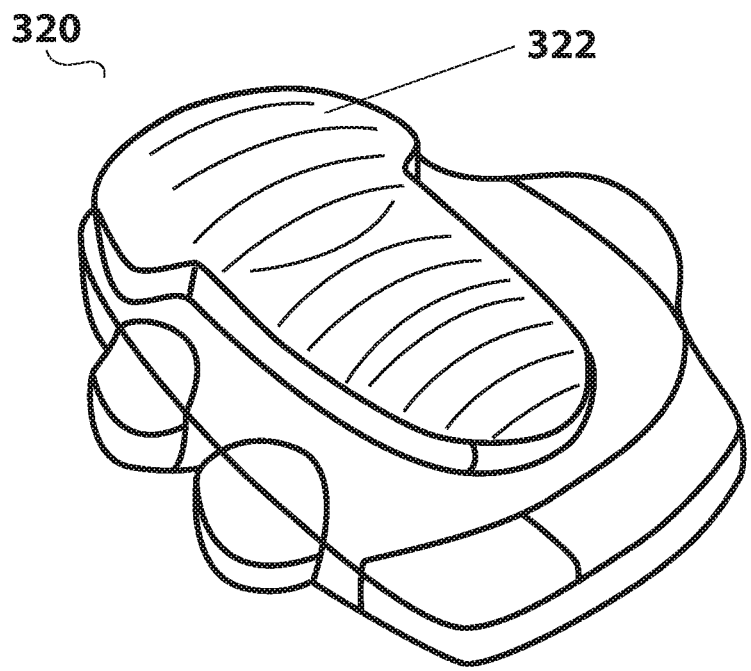
FIG. 21 is a perspective view of a foot controller for a robotic surgical system, according to one embodiment.

FIG. 21 depicts a foot controller 320, according to one embodiment. In this embodiment, the controller 320 has one pedal 322. Having a single pedal 322 eliminates the need for the user to release contact with the pedal 322 and make contact with one or more other pedals. In this embodiment, the pedal 322 is a multi-directional pedal 322 that acts like a joystick for the user's foot. The pedal can be moved in any of the four cardinal directions to activate a different function in relation to the surgical device or the surgical system.

Figure 22:
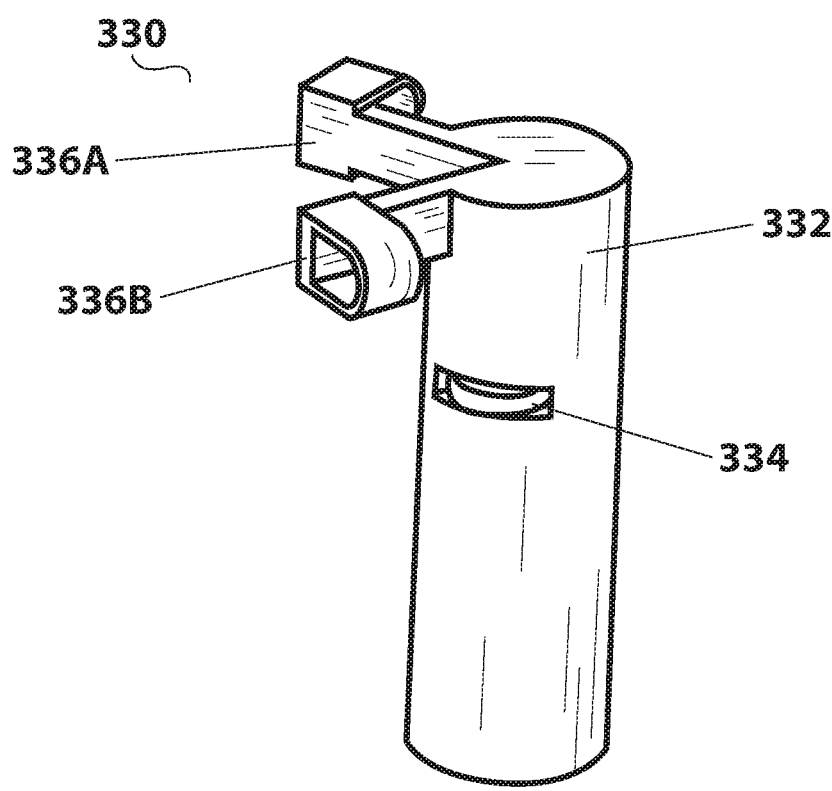
FIG. 22 is a perspective view of a handheld controller with a scroll wheel for a robotic surgical system, according to one embodiment.
Figure 23:
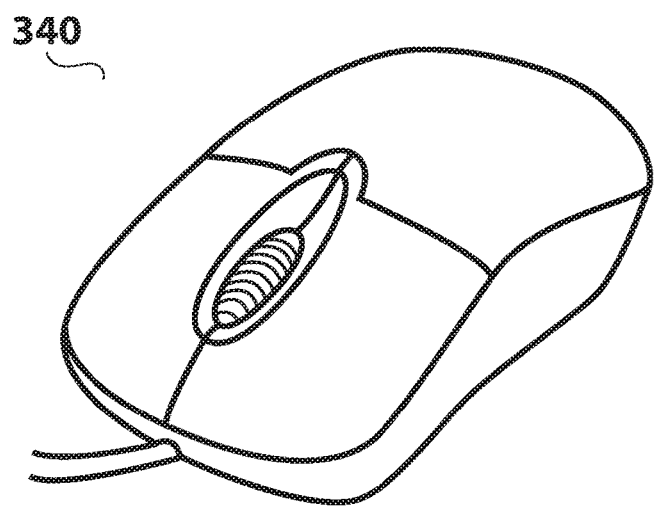
FIG. 23 is a perspective view of a standard mouse controller.

Alternatively, the foot controller can be configured to have multiple functions that are selectable via a hand- or finger-actuated button or input component. In one embodiment as shown in FIG. 22, the input component is a controller handle 330 with a scroll wheel 334, wherein the scroll wheel 334 can be actuated to select the desired function of a foot controller (such as the foot controller 320). Alternatively, as shown in FIG. 23, the input component can be a basic mouse 340. Regardless of the specific input component, the component 330 or 340 is operably coupled to the foot pedal (such as the foot controller 320 discussed above) such that the input component 330 or 340 can be used to select the function of the foot controller 320. In use, the user can use her or his hand to actuate the scroll wheel 332 of the handle 330 or the scroll wheel of the mouse 340 to select the appropriate function of the foot pedal, such as the foot controller 320. In one embodiment, a menu is displayed on a display or monitor of the controller when the user actuates the scroll wheel and the user can then select from that menu. Of course, this menu can apply to one foot controller (like the foot controller 320 above) or two different foot controllers or pedals.

In a further alternative, the controller has a pedal selection indicator that is displayed on the display. As an example, the pedal selection indicator could be an overlay on a display such as the user interface display 286 discussed above with respect to FIG. 16A. Alternatively, the indicator could be displayed in any known fashion on any known controller. In one embodiment, the pedal selection detecting device is a camera that is positioned to capture all of the one or more foot pedals associated with a foot controller. Alternatively, any sensor can be used that can detect which foot pedals are being used.

Returning to FIG. 22, the controller handle 330 can also be used to control any part of a surgical device or system. The handle 330 has a handle body 332, the scroll wheel 334, and two actuatable finger loops 336A, 336B. The scroll wheel 334 and both finger loops 336A, 336B can be actuated by a user to trigger certain actions by the system or the surgical device. One example of such an action relates to selection of a foot pedal function as described above, but many other actions can be accomplished via the wheel 334 and loops 336A, 336B. In use, the user grasps the handle body 332 and positions her or his hand such that the thumb and index finger can be positioned in the loops 336A, 336B and the middle finger is in close proximity with the scroll wheel 334 such that the middle finger can be used to actuate the wheel 334 as needed. It is understood that this scroll wheel 334 operates in a fashion similar to known scroll wheels, by providing both a scrolling action and a clicking action.

Returning to the surgical device embodiments discussed above, another set of surgical device implementations relate to devices having at least one biometric sensor associated with the device to monitor the status of the patient.

Figure 24:
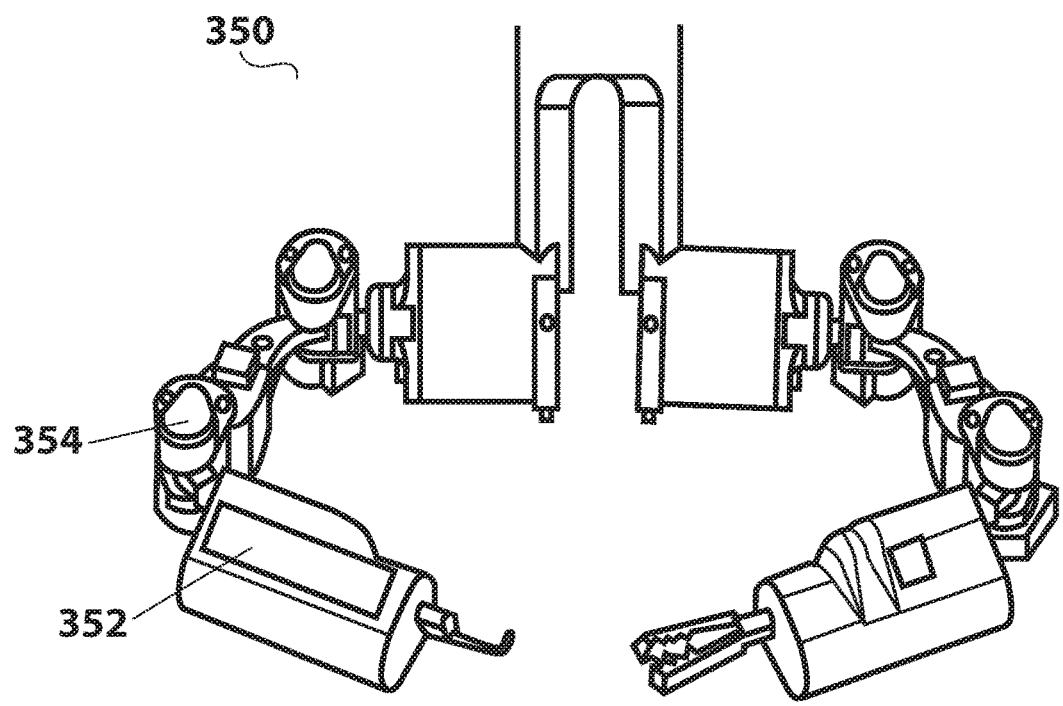
FIG. 24 is a perspective view of a robotic surgical device having at least one biometric sensor, according to one embodiment.

One example of a surgical device 350 embodiment having a biometric sensor 352 is set forth in FIG. 24. In this embodiment, the sensor 352 is positioned in an arm 354 of the device 350. Alternatively, the sensor 352 can be positioned anywhere else in or on the device 350. The sensor 352 can be coupled to or with the existing electronics in the arm 354 such that the sensor 352 is electrically coupled to an external controller and thereby can provide feedback regarding one or more biometric parameters. The various parameters can include, but are certainly not limited to, temperature, pressure, or humidity. In use, the biometric parameter(s) of interest can be monitored by using the sensor 352 (or two or more sensors) to capture the relevant data and transmit it to a controller that provides the information on a display for the user/surgeon to see.

Another set of embodiments relates to best practices in cavity insufflations. It is understood that a patient's surgical cavity is typically expanded for purposes of a surgical procedure in that cavity by insufflating the cavity with a gas to maximize the amount of space in the cavity while minimizing the risk of damaging the cavity wall or organs by inadvertent contact with the surgical tools. The gas most commonly used is carbon dioxide ("$CO_2$"). One problem with the use of $CO_2$ is the absorption of excess $CO_2$ into one or more tissues of the patient, which can cause or increase postoperative pain, including abdominal and shoulder pain. In one implementation, one method for maximizing insufflation while minimizing the problems of $CO_2$ absorption involves flushing the $CO_2$ from the patient's cavity at the completion of the surgical procedure. More specifically, once the procedure is complete, another gas (other than $CO_2$) is pumped into the patient's cavity, thereby forcing or "flushing" the $CO_2$ out of the cavity. In accordance with one implementation, the replacement or flushing gas can be a gas that is more reactive than $CO_2$, because the reactive gas is used after the procedure is complete (when risks of using such reactive gas is significantly reduced). In one embodiment, the replacement gas is oxygen ("$O_2$"). It is understood that the replacement gas is a gas that does not adversely affect the patient when the gas is absorbed.

EXAMPLE

One embodiment of a gross positioning system similar to those discussed above and depicted in FIGS. 14A and 14B was examined. In this specific example, the system was tested with a two armed surgical device with two and three degrees of freedom per arm. The degrees of freedom of each arm of the surgical device from proximal to distal tip were shoulder pitch, shoulder yaw, and elbow yaw. For the experiment, it was assumed the two arms would work within close proximity of one another, as in a stretch and dissect operation.

The benchtop experiment took place in a mock surgical environment at the University of Nebraska-Lincoln to show the advantages of the gross positioning system over a fixed stand-alone device. The known fundamentals of laparoscopic surgery (FLS) peg transfer task was used to demonstrate the dexterous workspace of the surgical device. The goal of this task was to touch the top of each peg.

The results of the benchtop testing with the gross positioning device show that the gross positioning system is advantageous for surgical devices that typically would have poor dexterity or limited workspace with such a positioning device. Without the positioning device, when all six degrees of freedom were used, the stand-alone device could only reach a portion of the maximum number of pegs. In contrast, when the gross positioning system was used, all of the pegs were reachable with the four and six DOF surgical devices. These benchtop results indicate the advantages of a gross positioning system coupled with restricted surgical devices.

Although the present invention has been described with reference to preferred embodiments, persons skilled in the art will recognize that changes may be made in form and detail without departing from the spirit and scope of the invention.

What is claimed is:

1. A gross positioning system for use with a robotic surgical device, the system comprising:
   (a) a body;
   (b) a first arm link operably coupled to the body at a first rotational joint;
   (c) a second arm link operably coupled to the first arm link at a second rotational joint; and
   (d) an extendable third arm link operably coupled to the second arm link, wherein at least a portion of the third arm link is rotatable about a third rotational joint, wherein the third arm link is configured to be positionable through an incision in a patient, the third arm link comprising a connection mechanism at a distal end of the third arm link, wherein the connection mechanism is configured to be coupleable to the robotic surgical device,
   wherein at least two of an axis of rotation of the first rotational joint, an axis of rotation of the second rotational joint, and an axis of rotation of the third rotational joint substantially intersect at a spherical joint.

2. The gross positioning system of claim 1, wherein the robotic surgical device comprises at least one arm, wherein the gross positioning system and robotic surgical device are configured to operate together to position the robotic surgical device within a body cavity of a patient.

3. The gross positioning system of claim 1, wherein the extendable third arm link comprises an extender body and an extendable rod slidably coupled to the extender body, wherein the extendable rod is configured to move between an extended position and a retracted position.

4. The gross positioning system of claim 1, wherein the spherical joint is disposed at the incision of the patient, wherein the third arm link is disposed through the spherical joint.

5. The gross positioning system of claim 1, wherein the connection mechanism is positionable in a body cavity of the patient.

6. A gross positioning system for use with a robotic surgical device, the system comprising:
   (a) a body;
   (b) a first arm link operably coupled to the body at a first rotational joint;
   (c) a second arm link operably coupled to the first arm link at a second rotational joint; and
   (d) an extendable third arm link operably coupled to the second arm link, wherein at least a portion of the third arm link is rotatable about a third rotational joint, wherein the third arm link is configured to be positionable through an incision in a patient, the third arm link comprising a connection mechanism at a distal end of the third arm link, wherein the connection mechanism is configured to be coupleable to the robotic surgical device,
   wherein at least one of an axis of rotation of the first rotational joint, an axis of rotation of the second rotational joint, and an axis of rotation of the third rotational joint is substantially perpendicular to at least one other of the axis of rotation of the first rotational joint, the axis of rotation of the second rotational joint, and the axis of rotation of the third rotational joint.

7. The gross positioning system of claim 6, wherein the extendable third arm link comprises an extender body and an extendable rod slidably coupled to the extender body, wherein the extendable rod is configured to move between an extended position and a retracted position.

8. The gross positioning system of claim 6, wherein the connection mechanism is positionable in a body cavity of the patient.

9. The gross positioning system of claim 6, wherein at least two of the axis of rotation of the first rotational joint, the axis of rotation of the second rotational joint, and the axis of rotation of the third rotational joint substantially intersect at a spherical joint.

10. The gross positioning system of claim 9, wherein the spherical joint is disposed at the incision of the patient, wherein the third arm link is disposed through the spherical joint.

11. An external gross positioning system for use with an internal robotic surgical device, the system comprising:
(a) a body;
(b) a first arm link operably coupled to the body at a first rotational joint;
(c) a second arm link operably coupled to the first arm link at a second rotational joint;
(d) an extendable third arm link operably coupled to the second arm link, wherein at least a portion of the third arm link is rotatable about a third rotational joint, the third arm link comprising a connection mechanism at a distal end of the third arm link, wherein the connection mechanism is configured to be coupleable to the robotic surgical device; and
(e) a spherical joint disposed substantially at an intersection of at least two of an axis of rotation of the first rotational joint, an axis of rotation of the second rotational joint, and an axis of rotation of the third rotational joint, wherein the spherical joint is disposed substantially at an insertion point of a patient, wherein the third arm link is disposed substantially through the spherical joint.

12. The gross positioning system of claim 11, wherein at least one of an axis of rotation of the first rotational joint, an axis of rotation of the second rotational joint, and an axis of rotation of the third rotational joint is substantially perpendicular to at least one other of the axis of rotation of the first rotational joint, the axis of rotation of the second rotational joint, and the axis of rotation of the third rotational joint.

13. The gross positioning system of claim 11, wherein the extendable third arm link comprises an extender body and an extendable rod slidably coupled to the extender body, wherein the extendable rod is configured to move between an extended position and a retracted position.

14. The gross positioning system of claim 11, wherein the connection mechanism is positionable in a body cavity of the patient.

15. A gross positioning system for use with a robotic surgical device, the system comprising:
(a) a body;
(c) a first arm link operably coupled to the body at a first rotational joint;
(d) a second arm link operably coupled to the first arm link at a second rotational joint;
(e) an extendable third arm link operably coupled to the second arm link, wherein at least a portion of the third arm link is rotatable about a third rotational joint, the third arm link comprising a connection mechanism at a distal end of the third arm link; and
(f) the robotic surgical device operably coupled to the connection mechanism, the robotic surgical device comprising:
(i) a device body;
(ii) a first arm operably coupled to the device body, the first arm comprising at least one first actuator; and
iii) a second arm operably coupled to the device body, the second arm comprising at least one second actuator,
wherein at least two of an axis of rotation of the first rotational joint, an axis of rotation of the second rotational joint, and an axis of rotation of the third rotational joint substantially intersect at a spherical joint.

16. The gross positioning system of claim 15, wherein at least one of an axis of rotation of the first rotational joint, an axis of rotation of the second rotational joint, and an axis of rotation of the third rotational joint is substantially perpendicular to at least one other of the axis of rotation of the first rotational joint, the axis of rotation of the second rotational joint, and the axis of rotation of the third rotational joint.

17. The gross positioning system of claim 15, wherein the extendable third arm link comprises an extender body and an extendable rod slidably coupled to the extender body, wherein the extendable rod is configured to move between an extended position and a retracted position.

18. The gross positioning system of claim 15, wherein the third arm link is configured to be positionable through an incision in a patient.

19. The gross positioning system of claim 15, wherein the spherical joint is disposed substantially at an insertion point of a patient, wherein the third arm link is disposed substantially through the spherical joint.

20. The gross positioning system of claim 15, wherein the connection mechanism is positionable in a body cavity of the patient.

* * * * *